(12) United States Patent
Jang et al.

(10) Patent No.: US 10,564,542 B2
(45) Date of Patent: Feb. 18, 2020

(54) PHOTORESIST COMPOSITIONS AND METHODS

(71) Applicant: Rohm and Haas Electronic Materials Korea Ltd., Cheonan, Chungcheongnam-Do (KR)

(72) Inventors: Min-Kyung Jang, Chungcheongnam-Do (KR); Eui-Hyun Ryu, Chungcheongnam-Do (KR); Chang-Young Hong, Chungcheongnam-Do (KR); Dong-Yong Kim, Chungcheongnam-Do (KR)

(*) Notice: Subject to any disclaimer, the term of this patent is extended or adjusted under 35 U.S.C. 154(b) by 0 days.

(21) Appl. No.: 15/281,492

(22) Filed: Sep. 30, 2016

(65) Prior Publication Data
US 2017/0090283 A1    Mar. 30, 2017

Related U.S. Application Data

(60) Provisional application No. 62/235,363, filed on Sep. 30, 2015.

(51) Int. Cl.
| | |
|---|---|
| *G03F 7/004* | (2006.01) |
| *C08F 220/26* | (2006.01) |
| *C08F 220/34* | (2006.01) |
| *C07C 271/12* | (2006.01) |
| *C07D 211/48* | (2006.01) |
| *C08F 220/36* | (2006.01) |
| *G03F 7/038* | (2006.01) |
| *G03F 7/16* | (2006.01) |
| *G03F 7/20* | (2006.01) |
| *G03F 7/32* | (2006.01) |
| *G03F 7/40* | (2006.01) |

(52) U.S. Cl.
CPC .......... *G03F 7/0045* (2013.01); *C07C 271/12* (2013.01); *C07D 211/48* (2013.01); *C08F 220/26* (2013.01); *C08F 220/34* (2013.01); *C08F 220/36* (2013.01); *G03F 7/038* (2013.01); *G03F 7/162* (2013.01); *G03F 7/20* (2013.01); *G03F 7/325* (2013.01); *G03F 7/40* (2013.01); *C08F 2220/365* (2013.01)

(58) Field of Classification Search
CPC .......... G03F 7/004; G03F 7/30; G03F 7/0045; G03F 7/038; G03F 7/40; C08F 220/34; C08F 220/26; C08F 220/365; C08F 2220/365

USPC ..... 430/270.1, 322, 325, 329, 913; 526/258, 526/307.2
See application file for complete search history.

(56) References Cited

U.S. PATENT DOCUMENTS

| | | | |
|---|---|---|---|
| 6,790,579 B1 | 9/2004 | Goodall et al. | |
| 8,507,175 B2* | 8/2013 | Hatakeyama | G03F 7/0045 430/270.1 |
| 8,722,825 B2* | 5/2014 | Wang | G03F 7/0045 430/270.1 |
| 9,012,128 B2* | 4/2015 | Wang | G03F 7/0045 430/270.1 |
| 2006/0172149 A1 | 8/2006 | Ahn et al. | |
| 2007/0190451 A1 | 8/2007 | Ishii et al. | |
| 2012/0282548 A1* | 11/2012 | Enomoto | G03F 7/0045 430/284.1 |
| 2013/0144057 A1* | 6/2013 | Morita | C07C 271/12 544/172 |
| 2013/0177853 A1 | 7/2013 | Shimizu et al. | |
| 2013/0186292 A1* | 7/2013 | Ushijima | C08G 18/8116 101/395 |
| 2013/0344436 A1 | 12/2013 | Nakamura et al. | |
| 2014/0038102 A1 | 2/2014 | Park et al. | |

FOREIGN PATENT DOCUMENTS

| | | | | |
|---|---|---|---|---|
| EP | 1702962 B1 | | 12/2008 | |
| JP | H111337722 A | | 12/1999 | |
| JP | 2006308701 A | * | 11/2006 | |
| JP | 2009031767 A | * | 2/2009 | .......... G03F 7/0046 |
| JP | 2009292886 A | * | 12/2009 | |
| JP | 2010047668 A | * | 3/2010 | |
| JP | 2013105163 A | * | 5/2013 | ............. G03F 7/004 |
| JP | 2015129939 A | * | 7/2015 | ............... G03F 7/38 |
| KR | 20070015665 A | * | 2/2007 | |

OTHER PUBLICATIONS

Machine translation of KR 2007-015665 (no date).*
Machine translation of JP 2010-047668 (no date).*
Machine translation of JP 2015-129939 (no date).*
Machine translation of JP 2013-105163 (no date).*
Machine translation of JP 2009-031767 (no date).*

* cited by examiner

*Primary Examiner* — Amanda C. Walke
(74) *Attorney, Agent, or Firm* — Mintz Levin Cohn Ferris Glovsky and Popeo, P.C.; Peter F. Corless

(57) ABSTRACT

New photoresists are provided that are useful in a variety of applications, including negative-tone development processes. Preferred resists comprise a first polymer comprising first units comprising a reactive nitrogen-containing moiety spaced from the polymer backbone, wherein the nitrogen-containing moiety produces a basic cleavage product during lithographic processing of the photoresist composition.

11 Claims, No Drawings

PHOTORESIST COMPOSITIONS AND METHODS

CROSS-REFERENCE TO RELATED APPLICATION

This application claims priority to U.S. Provisional Application No. 62/235,363, filed Sep. 30, 2015. The contents of the foregoing application is incorporated herein by reference in its entirety.

BACKGROUND

The invention relates generally to the manufacture of electronic devices. More specifically, this invention relates to photoresist compositions and to photolithographic processes which allow for the formation of fine patterns using a negative tone development process.

Photoresists are photosensitive films used for the transfer of images to a substrate. A coating layer of a photoresist is formed on a substrate and the photoresist layer is then exposed through a photomask to a source of activating radiation. Following exposure, the photoresist is developed to provide a relief image that permits selective processing of a substrate.

Considerable effort has been made to extend the practical resolution capabilities of positive tone resist development, including in immersion lithography. One such example involves negative tone development (NTD) of a traditionally positive-type chemically amplified photoresist through use of particular developers, typically organic developers such as ketones, esters or ethers, leaving behind a pattern created by the insoluble exposed regions. See, for instance, U.S. Pat. No. 6,790,579.

Certain problems however can result with use of NTD processes. For instance, the relative UV intensity through a resist coating layer is decreased from upper to lower layer regions and from iso contant holes (C/Hs) to dense contact holes (C/Hs). In turn, the concentration of photo-generated acid also varies through a resist layer (acid will be present in decreased amounts in lower resist layer regions) and will vary from iso C/Hs to dense C/Hs. As a result, pattern profiles will exhibit undesirable T-top shapes, pattern collapse and missing contact holes may occur, and iso-dense bias and depth of focus margins may be at unacceptable levels.

Certain basic additives have been employed to attempt to improve resist resolution. See JPH11337722A; US2007190451; EP1702962B1; US20060172149; US20130177853; US20130344436; and US20140038102.

Electronic device manufacturers continually seek increased resolution of a patterned photoresist image. It would be desirable to have new photoresist compositions that could provide enhanced imaging capabilities.

SUMMARY

We now provide new photoresists that are useful in a variety of applications, including negative-tone development processes.

More particularly, in a preferred aspect, photoresist compositions are provided that comprise: (a) a first polymer comprising first units comprising a reactive nitrogen-containing moiety spaced from the polymer backbone, wherein the nitrogen-containing moiety produces a basic cleavage product during lithographic processing of the photoresist composition; and (b) one or more acid generators.

As referred to herein, a basic cleavage product includes moieties that include one or more nitrogen atoms. A basic cleavage product can be produced as a basic moiety (e.g. moiety with one or more nitrogen atoms) is cleaved (i.e. covalent bond breakage) from the first polymer through reaction of an acid-labile group in the optional presence of an acid generator and optional thermal treatment (e.g. post-exposure bake).

The reactive nitrogen-containing moiety can be spaced from the polymer backbone by any of a number of groups including for example alkyl (alkylene); a ring group comprising carbon atoms; and and/or hetero atoms such as oxygen or optionally substituted sulfur (e.g. S(O), S(O)$_2$), in a chain that comprises 1 or more atoms (including carbon atoms), generally 1, 2, 3, 4, 5, 6, 7, 8, 9 or 10 atoms (including carbon atoms), interposed between the polymer backbone and the reactive nitrogen-containing moiety.

As understood, the term polymer backbone refers to the series of covalently bonded atoms that together create the continuous linear chain of the polymer. In poly(acrylate) or poly(alkylacrylate) (such as poly(methacrylate) resins, the reactive nitrogen-containing moiety can be spaced from the polymerized acrylate carboxy (—CH$_2$—CH(COO—)—) moiety or alkylacrylate carboxy (—CH$_2$—C(alkyl)(COO—)—) moiety by 1 or more atoms (including carbon atoms), generally 1, 2, 3, 4, 5, 6, 7, 8, 9 or 10 atoms (including carbon atoms).

In certain preferred aspects, 1, 2, 3, 4 or 5 optionally substituted carbon atoms (spacer group) may be interposed between a polymerized acrylate or alkylacrylate (such as methacrylate) polymer backbone moiety and a reactive nitrogen-containing moiety such as carbamate (e.g. spacer group interposed between and linked to 1) acrylate or alkylacrylate moiety and 2) —O(C=O)—N< or >N(=O)O—).

In certain preferred aspects, 1, 2, 3, 4 or 5 optionally substituted carbon atoms (spacer group) may be interposed between a polymerized acrylate or alkylacrylate (such as methacrylate) polymer backbone moiety and a reactive nitrogen-containing moiety such as carbamate (e.g. spacer group interposed between and linked to 1) acrylate/alkylacrylate moiety and 2) —O(C=O)—N< or >N(=O)O—). Such preferred spacer groups may be part of a non-cyclic chain or a cyclic group where the cyclic group may or may not contain a nitrogen (e.g. a nitrogen of a carbamate group) as a ring member. Such preferred spacer groups also may be optionally substituted, for example one or more of the interposed carbon atoms of the spacer group may be substituted by one or more alkyl groups such as C$_{1-12}$alkyl including methyl, or a cyclic alkyl such as cyclohexyl, or by another ring member carbon.

An acid-labile moiety such as an acid-labile ester or acetal group also may be preferably interposed between a polymer backbone and the reactive nitrogen-containing moiety. For instance, in one preferred aspect, a photoacid ester (particularly, ester substituted with quaternary carbon, i.e. —C(=O)OY where Y is a quaternary carbon) is interposed between the polymer backbone and a reactive nitrogen-containing moiety.

Preferably, the first polymer further comprises second units each comprising 1) a reactive nitrogen-containing moiety and 2) an acid-labile group. Also preferably, the nitrogen-containing moiety is spaced from the polymer by optionally substituted alkylene, optionally substituted carbon alicyclic, optionally substituted heteroalicyclic, optionally substituted carbocyclic aryl or optionally substituted heteroaryl.

In additional preferred aspects, the first polymer further comprises third units that 1) comprise one or more hydrophobic groups and 2) are distinct from both of the first and second units.

In certain preferred aspects, the nitrogen-containing moiety is a protected amine. For instance, the nitrogen-containing moiety is suitably a carbamate or sulfamate.

In an additional preferred aspect, photoresist compositions are provided that comprise (a) a polymer comprising: units comprising 1) a reactive nitrogen-containing moiety spaced from the polymer backbone, wherein the nitrogen-containing moiety produces a basic cleavage product during lithographic processing of the photoresist composition and 2) an acid-labile group; and (b) one or more acid generators.

In certain preferred aspects, the present photoresists may comprise an additional polymer (second polymer). The second polymer suitably may comprise acid-labile group. As further discussed below, in certain embodiments, the first and second polymers may have differing surface energies.

In certain preferred aspects, the first polymer may further comprise third units that (1) comprise one or more hydrophobic groups and (2) are distinct from the first and second units. Suitably, the one or more hydrophobic groups of the second units and, if present third units, each comprise 3, 4, 5, 6, 7, 8 or more carbon atoms.

Preferably, prior to lithographic processing, the nitrogen-containing moiety of the first polymer is a protected amine which can be can be deprotected in the presence of acid produced during lithographic processing. For instance, the acid may be generated from one or more photoacid generators and/or thermal acid generators present in photoresist composition that generate acid during exposure and/or post-exposure bake processing steps of a coating layer of the photoresist composition.

Typically, such a deprotected nitrogen will be significantly more basic than the same nitrogen in protected form prior to lithographic processing. For instance, the pKa differential between 1) the nitrogen-containing moiety prior to lithographic processing and 2) the nitrogen-containing moiety upon deprotection in the presence of acid during lithographic processing suitably may be from 1 to 2, 3, 4, 5, 6, 7, 8, 9, 10, 11, 12, 13 or 14 or more.

In certain additional preferred aspects, in a first polymer of a photoresist composition, the (i) units that comprise a nitrogen-containing moiety also further comprise a hydrophobic group. For instance, the acid-labile moiety of the protected nitrogen moiety may comprise a hydrophobic group such as an optionally substituted straight, branched or cyclic alkyl having 3, 4, 5, 6, 7, 8, 9, 10 or more carbons, e.g. isopropyl, t-butyl, sec-pentyl, adamantyl including methyladamntyl and 1-ethylcyclopentyl.

According to a further aspect, coated substrates are provided. The coated substrates comprise a substrate and a layer of a photoresist composition of the invention over a surface of the substrate.

According to a yet further aspect, methods of forming a photolithographic pattern are provided. The methods suitably comprise: (a) providing a substrate comprising one or more layers to be patterned over a surface of the substrate; (b) applying a layer of a photoresist composition of the invention over the one or more layers to be patterned; (c) patternwise exposing the photoresist composition layer to activating radiation; and (d) applying a developer to the photoresist composition layer to thereby produce a resist relief image. Suitably, the exposed photoresist composition layer is thermally treated in a post-exposure bake process prior to development. In preferred aspects, an acid-labile group of a nitrogen-containing moiety of a first polymer of the photoresist composition will undergo reaction during the exposing and a post-exposure, pre-developing thermal treatment to provide an amine linked to the first polymer.

In a preferred aspect, unexposed portions of the photoresist layer are removed by the developer, leaving a photoresist pattern over the one or more layer to be patterned. The patternwise exposing can be conducted by immersion lithography or, alternatively, using dry exposure techniques. In certain aspects, implant and EUV lithography processes are also preferred.

The invention also includes polymers that comprise a reactive nitrogen-containing moiety spaced from the polymer backbone, wherein the nitrogen-containing moiety produces a basic cleavage product during lithographic processing of the photoresist composition.

Electronic devices formed by the disclosed methods are also provided, including devices formed by the disclosed negative tone development processes.

References herein to pKa values of nitrogen-containing groups or other groups designate values determined by Taft parameter analysis, as such analysis is known in this field and described in J. Cameron et al., "Structural Effects of Photoacid Generators on Deep UV Resist Performance," Society of Plastic Engineers, Inc. Proceedings, "Photopolymers, Principles, Processes and Materials, 11$^{th}$ International Conference, pp. 120-139 (1997); and J. P. Gutthrie, Can. J Chem., 56:2342-2354 (1978).

As used herein, the articles "a" and "an" are inclusive of one or more unless otherwise indicated expressly or by context.

Other aspects of the invention are disclosed infra.

DETAILED DESCRIPTION

As discussed, photoresist compositions of the invention are particularly suitable for use in negative tone development processes. Particularly preferred photoresist compositions of the invention when used in a negative tone development process provide one or preferably more of improved focus latitude and exposure latitude, resist patterns such as lines and contact holes which are uniform in geometry, and reduced defectivity.

In preferred compositions, the first polymer can migrate toward the upper surface of the resist coating layer during coating of the photoresist composition. In certain systems, this can form a surface layer substantially made up of the first polymer. Without being bound by any theory, the nitrogen (basic) moiety of the first polymer is believed to contribute to the control of scattered or stray light, thereby allowing for reduction in patterning defects such as missing contact holes and micro-bridging defects in the case of line and trench pattern formation. Following exposure and post exposure bake (PEB), the resist coating layer can be developed, including in a developer comprising an organic solvent. The organic developer removes unexposed regions of the photoresist layer and the surface layer of the exposed regions. Benefits of the inventive photoresist compositions can be achieved when using the compositions in dry lithography or immersion lithography processes. When used in immersion lithography, preferred photoresist compositions can further exhibit reduced migration (leaching) of photoresist materials into an immersion fluid also a result of the additive polymer's migration to the resist surface. Significantly, this can be achieved without use of a topcoat layer over the photoresist.

The photoresists can be used at a variety of radiation wavelengths, for example, wavelengths of sub-400 nm, sub-300 or sub-200 nm, or with 248 nm, 193 nm and EUV (e.g., 13.5 nm) exposure wavelengths being preferred. The compositions can further be used in electron beam (E-beam) exposure processes.

The photoresist compositions of the invention are preferably chemically-amplified materials. In preferred embodiments, the photoresist compositions comprise one or more second or matrix polymers (distinct from the first polymer) that comprise an acid labile group. The acid labile group is a chemical moiety that readily undergoes deprotection reaction in the presence of an acid. The second or matrix polymer as part of a layer of the photoresist composition undergoes a change in solubility in a developer described herein as a result of reaction with acid generated from the photoacid and/or thermal acid generator during lithographic processing, particularly following softbake, exposure to activating radiation and post exposure bake. This results from photoacid-induced cleavage of the acid labile group, causing a change in polarity of the second polymer. The acid labile group can be chosen, for example, from tertiary alkyl carbonates, tertiary alkyl esters, tertiary alkyl ethers, acetals and ketals. Preferably, the acid labile group is an ester group that contains a tertiary non-cyclic alkyl carbon or a tertiary alicyclic carbon covalently linked to a carboxyl oxygen of an ester of the second matrix polymer. The cleavage of such acid labile groups results in the formation of carboxylic acid groups. Suitable acid labile-group containing units include, for example, acid-labile (alkyl)acrylate units, such as t-butyl (meth)acrylate, 1-methylcyclopentyl (meth)acrylate, 1-ethylcyclopentyl (meth)acrylate, 1-isopropylcyclopentyl (meth)acrylate, 1-propylcyclopentyl (meth)acrylate, 1-methylcyclohexyl (meth)acrylate, 1-ethylcyclohexyl (meth)acrylate, 1-isopropylcyclohexyl (meth)acrylate, 1-propylcyclohexyl (meth)acrylate, t-butyl methyladamantyl(meth)acrylate, ethylfenchyl(meth)acrylate, and the like, and other cyclic, including alicyclic, and non-cyclic (alkyl) acrylates. Acetal and ketal acid labile groups can be substituted for the hydrogen atom at the terminal of an alkali-soluble group such as a carboxyl group or hydroxyl group, so as to be bonded with an oxygen atom. When acid is generated, the acid cleaves the bond between the acetal or ketal group and the oxygen atom to which the acetal-type acid-dissociable, dissolution-inhibiting group is bonded. Exemplary such acid labile groups are described, for example, in U.S. Pat. Nos. 6,057,083, 6,136,501 and 8,206,886 and European Pat. Pub. Nos. EP01008913A1 and EP00930542A1. Also suitable are acetal and ketal groups as part of sugar derivative structures, the cleavage of which would result in the formation of hydroxyl groups, for example, those described in U.S. Patent Application No. US2012/0064456A1.

For imaging at wavelengths of 200 nm or greater such as 248 nm, suitable resin materials (including for use as second polymers of the present photoresist compositions) include, for example, phenolic resins that contain acid-labile groups. Particularly preferred resins of this class include: (i) polymers that contain polymerized units of a vinyl phenol and an acid labile (alkyl) acrylate as described above, such as polymers described in U.S. Pat. Nos. 6,042,997 and 5,492,793; (ii) polymers that contain polymerized units of a vinyl phenol, an optionally substituted vinyl phenyl (e.g., styrene) that does not contain a hydroxy or carboxy ring substituent, and an acid labile (alkyl) acrylate such as described above, such as polymers described in U.S. Pat. No. 6,042,997; (iii) polymers that contain repeat units that comprise an acetal or ketal moiety that will react with photoacid, and optionally aromatic repeat units such as phenyl or phenolic groups; such polymers described in U.S. Pat. Nos. 5,929,176 and 6,090,526, and blends of (i) and/or (ii) and/or (iii).

For imaging at certain sub-200 nm wavelengths such as 193 nm, the second or matrix polymer is typically substantially free (e.g., less than 15 mole %), preferably completely free, of phenyl, benzyl or other aromatic groups where such groups are highly absorbing of the radiation. Suitable polymers that are substantially or completely free of aromatic groups are disclosed in European Patent Publication No. EP930542A1 and U.S. Pat. Nos. 6,692,888 and 6,680,159.

Other suitable second or matrix polymers include, for example, those which contain polymerized units of a non-aromatic cyclic olefin (endocyclic double bond) such as an optionally substituted norbornene, for example, polymers described in U.S. Pat. Nos. 5,843,624 and 6,048,664. Still other suitable matrix polymers include polymers that contain polymerized anhydride units, particularly polymerized maleic anhydride and/or itaconic anhydride units, such as disclosed in European Published Application EP01008913A1 and U.S. Pat. No. 6,048,662.

Also suitable as the second or matrix polymer is a resin that contains repeat units that contain a hetero atom, particularly oxygen and/or sulfur (but other than an anhydride, i.e., the unit does not contain a keto ring atom). The heteroalicyclic unit can be fused to the polymer backbone, and can comprise a fused carbon alicyclic unit such as provided by polymerization of a norbornene group and/or an anhydride unit such as provided by polymerization of a maleic anhydride or itaconic anhydride. Such polymers are disclosed in International Pub. No. WO0186353A1 and U.S. Pat. No. 6,306,554. Other suitable hetero-atom group containing matrix polymers include polymers that contain polymerized carbocyclic aryl units substituted with one or more hetero-atom (e.g., oxygen or sulfur) containing groups, for example, hydroxy naphthyl groups, such as disclosed in U.S. Pat. No. 7,244,542.

In the case of sub-200 nm wavelengths such as 193 nm and EUV (e.g., 13.5 nm), the second or matrix polymer may include a unit containing a lactone moiety for controlling the dissolution rate of the second matrix polymer and photoresist composition. Suitable monomers for use in the second or matrix polymer containing a lactone moiety include, for example, the following:

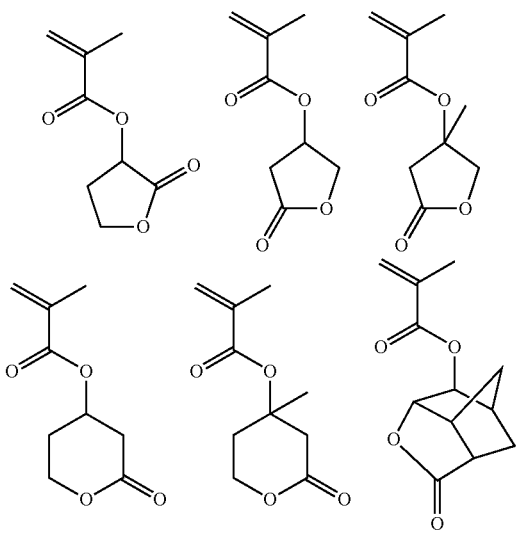

-continued

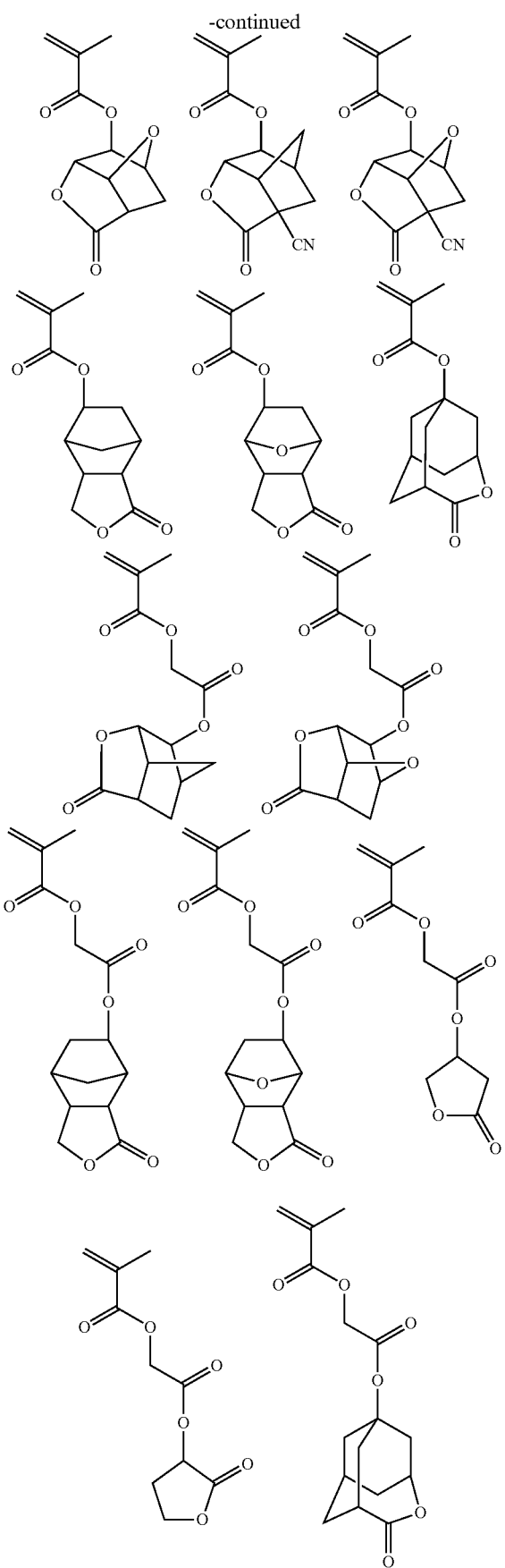

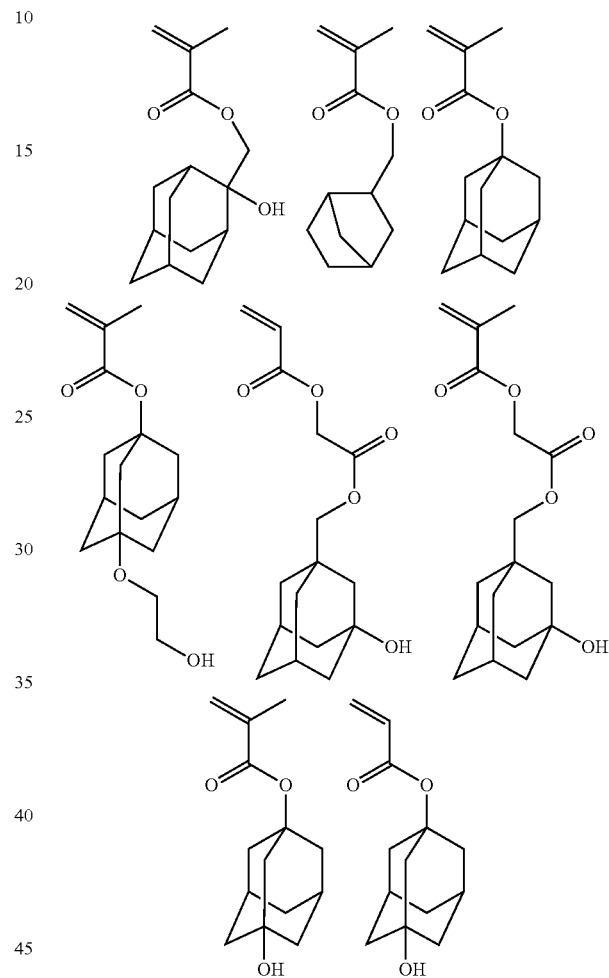

Such a second or matrix polymer further typically includes a unit containing a polar group, which enhances etch resistance of the matrix polymer and photoresist composition and provides additional means to control the dissolution rate of the matrix polymer and photoresist composition. Monomers for forming such a unit include, for example, the following:

The second or matrix polymer can include one or more additional units of the types described above. Typically, the additional units for the second or matrix polymer will include the same or similar polymerizable group as those used for the monomers used to form the other units of the polymer, but may include other, different polymerizable groups in the same polymer backbone.

In preferred aspects, the second or matrix polymer has a higher surface energy than that of the first or additive polymer, described below, and should be substantially non-miscible with the second polymer. As a result of the difference in surface energies, segregation of the second polymer from the first polymer can take place during spin-coating. A suitable surface energy of the second or matrix polymer is typically from 20 to 50 mN/m, preferably from 30 to 40 mN/m.

While not to be limited thereto, exemplary second or matrix polymers include, for example, the following:

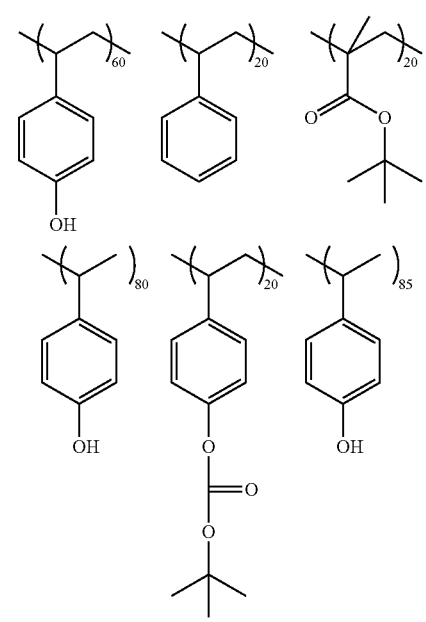
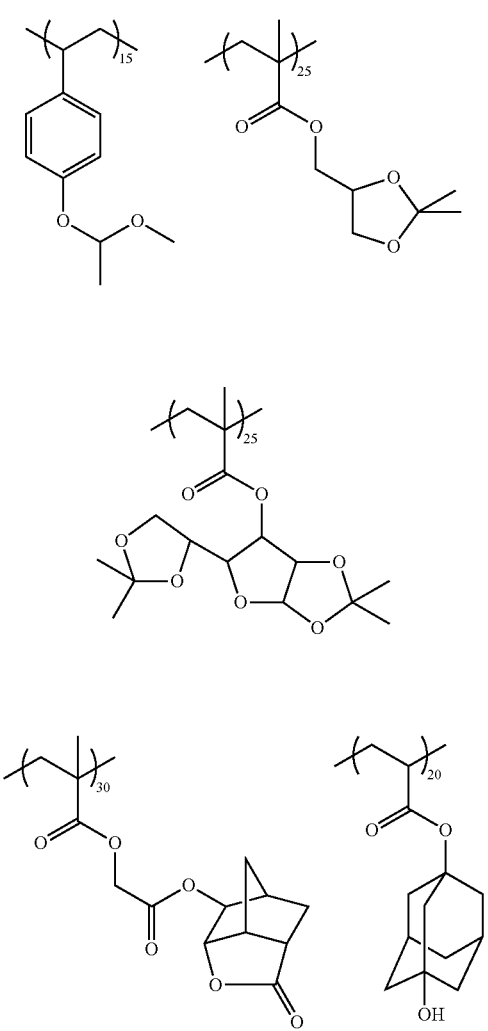
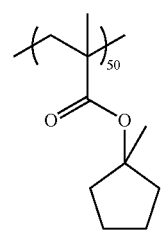
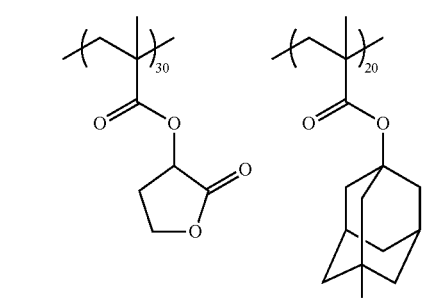
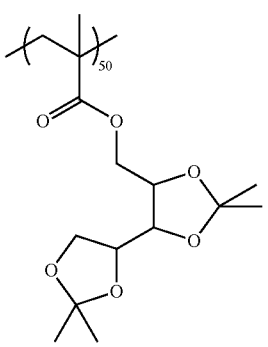
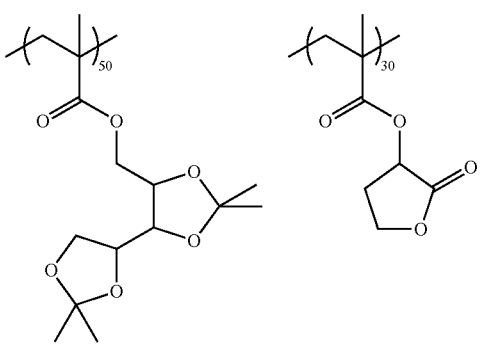
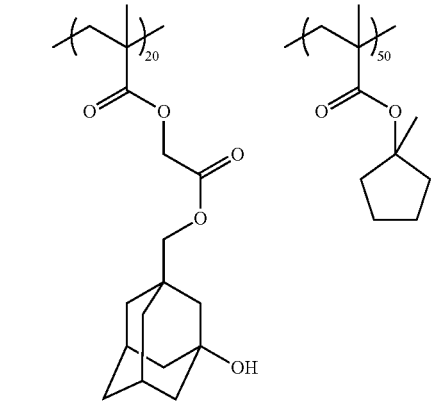
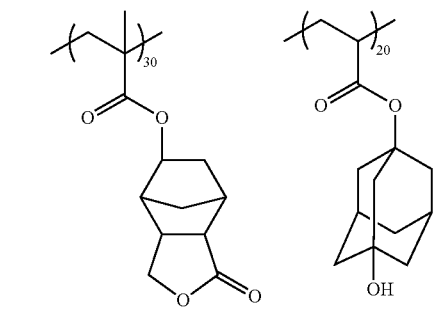

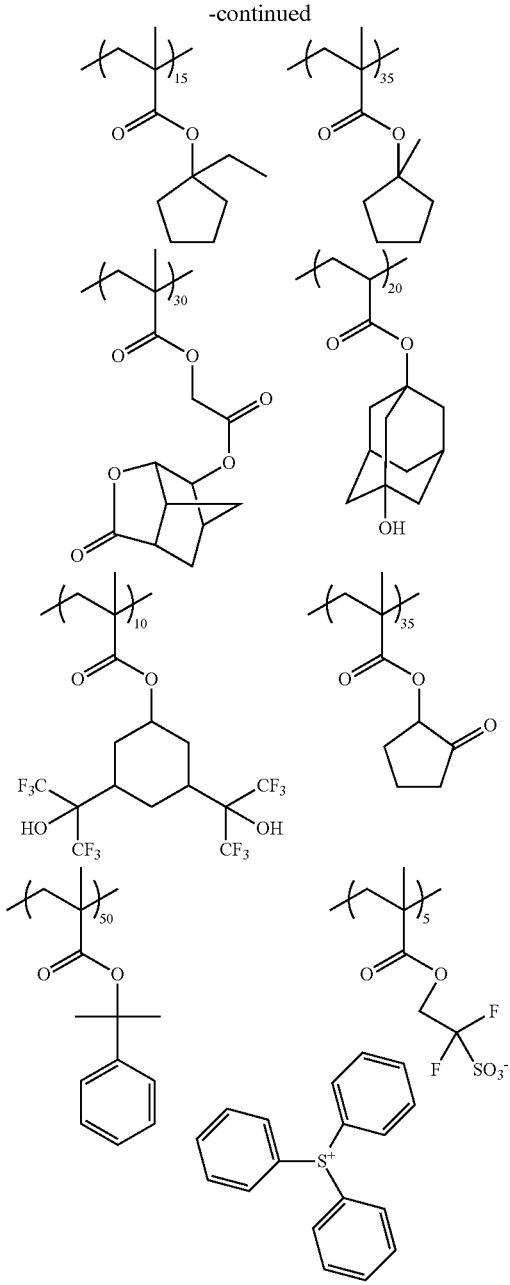

Suitable second or matrix polymers for use in the photoresist compositions of the invention are commercially available and can readily be made by persons skilled in the art. The second polymer is present in the resist composition in an amount sufficient to render an exposed coating layer of the resist developable in a suitable developer solution. Typically, the second polymer is present in the composition in an amount of from 50 to 95 wt % based on total solids of the resist composition. The weight average molecular weight $M_w$ of the second polymer is typically less than 100,000, for example, from 3000 to 100,000, more typically from 3000 to 15,000. Blends of two or more of the above-described second polymers can suitably be used in the photoresist compositions of the invention.

The first or additive polymer is preferably a material that has a lower surface energy than that of the second polymer and should be substantially non-miscible with the second polymer. In this way, segregation or migration of the first polymer to the top or upper portions of an applied photoresist layer during the coating process is facilitated. While the desired surface energy of the first polymer will depend on the particular second polymer and its surface energy, the first polymer surface energy is typically from 18 to 40 mN/m, preferably from 20 to 35 mN/m and more preferably from 29 to 33 mN/m. While the first polymer migrates to the upper surface of the resist layer during the coating process, it is preferable that there be some intermixing between the first polymer and second or matrix polymer immediately beneath the resist layer surface. Such intermixing is believed to aid in reducing surface inhibition in the resist layer by reduction or elimination of the acid generated in dark regions in the vicinity of the second or matrix polymer due to stray light. The extent of intermixing will depend, for example, on the difference in surface energy (SE) between the second or matrix polymer (MP) and first or additive polymer (AP) ($\Delta SE = SE_{MP} - SE_{AP}$). For given first or matrix and second or additive polymers, the degree of intermixing can be increased with reduced $\Delta SE$. The $\Delta SE$ is typically from 2 to 32 mN/m, preferably from 5 to 15 mN/m.

As discussed, the first or additive polymers useful in the photoresist compositions are copolymers that have a plurality of distinct repeat units, for example, two, three or four distinct repeat units.

The first polymer is preferably free of silicon. Silicon-containing polymers exhibit a significantly lower etch rate than organic photoresist polymers in certain etchants. As a result, aggregation of a silicon-containing first polymer at the surface of an organic second polymer-based resist layer can cause cone defects during the etching process. The first polymer may contain fluorine or can be free of fluorine. Preferred first polymers are soluble in the same organic solvent(s) used to formulate the photoresist composition. Preferred first polymers also will be soluble or become soluble upon post exposure bake (e.g., 120° C. for 60 seconds) in organic developers used in negative tone development processes.

As discussed, the first polymer preferably may contain a unit formed from one or more monomer corresponding to the following Formula (I):

$$X_1—R_1—X_2—R_2—X_3 \qquad (I)$$

wherein $X_1$ is a polymerizable functional group such as an acrylate or alkylacrylate such as a methacrylate; $R_1$ may be an optionally substituted linear, branched or cyclic aliphatic group or an aromatic group, suitably $C_{1-15}$ alkyl and optionally fluorinated; $X_2$ is a basic moiety such as a nitrogen and may be a component of or taken together with $R_1$ (e.g. $R_1$ and $X_2$ may combine to form a piperdinyl moiety); $R_2$ is an acid labile group; and $X_3$ may be optionally substituted linear, branched or cyclic aliphatic group or an aromatic group.

The polymerizable functional group $X_1$ can be chosen, for example, from the following general formulae (P-1), (P-2) and (P-3):

(P-1)

wherein $R_2$ is chosen from hydrogen, fluorine and fluorinated and non-fluorinated C1 to C3 alkyl; and X is oxygen or sulfur;
(P-2)
wherein $R_3$ is chosen from hydrogen, fluorine and fluorinated and non-fluorinated C1 to C3 alkyl; and
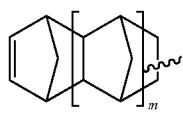
(P-3)
wherein m is an integer from 0 to 3.
Exemplary suitable monomers are described below, but are not limited to these structures.
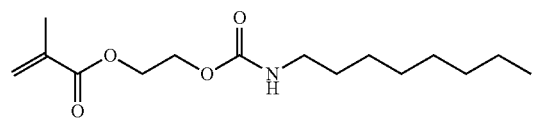
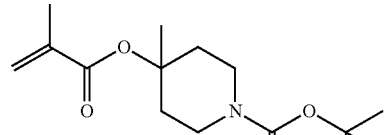
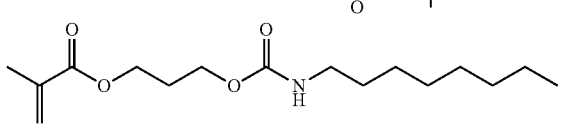
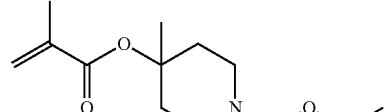
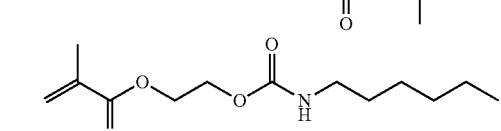
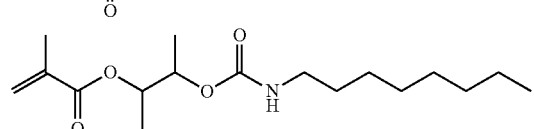
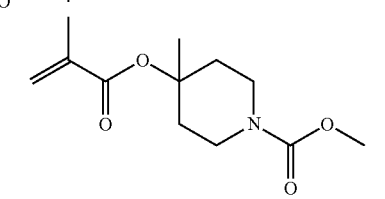
-continued
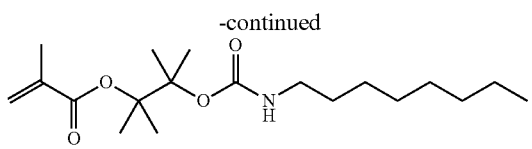
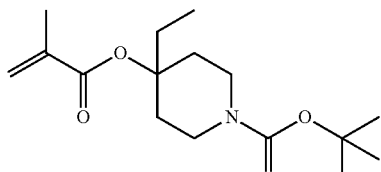
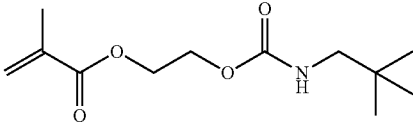
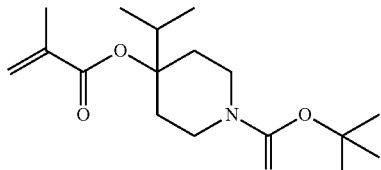
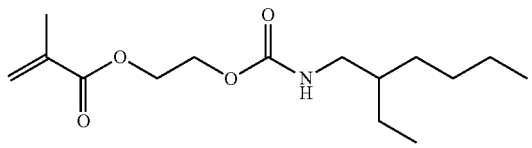
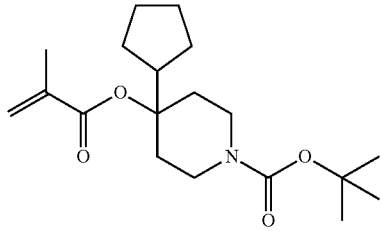
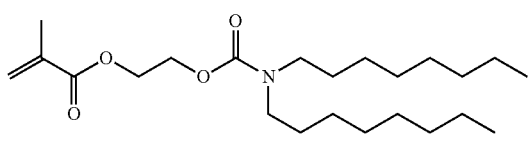
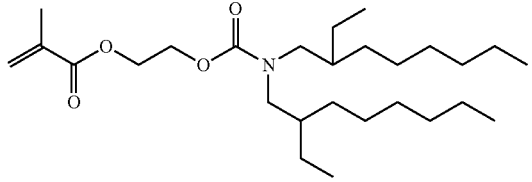
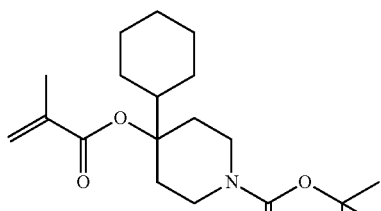
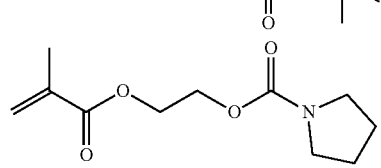

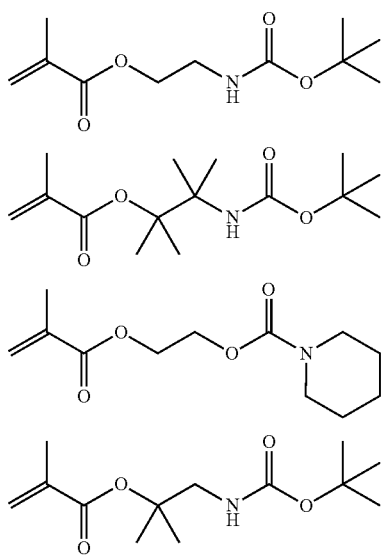

Preferably, the first polymer also comprises one or more additional distinct units (second units) formed from monomers corresponding to the following general formula (I-1):

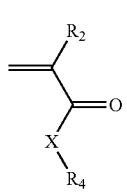

(I-1)

wherein: $R_2$ is chosen from hydrogen, fluorine and fluorinated and non-fluorinated C1 to C3 alkyl; and X is oxygen or sulfur; and $R_4$ is chosen from substituted and unsubstituted C1 to C20 linear, branched and cyclic hydrocarbons, preferably fluorinated and non-fluorinated C1 to C15 alkyl, more preferably fluorinated and non-fluorinated C3 to C8 alkyl and most preferably fluorinated and non-fluorinated C4 to C5 alkyl, with $R_4$ preferably being branched to provide a higher water receding contact angle when used in immersion lithography, and $R_4$ substitutions of haloalkyl and haloalcohol such as fluoroalkyl and fluoroalcohol being suitable.

As discussed, various moieties of monomers, polymers and other materials may be optionally substituted (or stated to be "substituted or unsubstituted"). A "substituted" substituent may be substituted at one or more available positions, typically 1, 2, or 3 positions by one or more suitable groups such as e.g. halogen (particularly F, Cl or Br); cyano; nitro; $C_{1-8}$ alkyl; $C_{1-8}$ alkoxy; $C_{1-8}$ alkylthio; $C_{1-8}$ alkylsulfonyl; $C_{2-8}$ alkenyl; $C_{2-8}$ alkynyl; hydroxyl; nitro; alkanoyl such as a $C_{1-6}$ alkanoyl e.g. acyl, haloalkyl particularly $C_{1-8}$ haloalkyl such as $CF_3$; —CONHR, —CONRR' where R and R' are optionally substituted $C_{1-8}$alkyl; —COOH, COC, >C=O; and the like.

Exemplary suitable monomers of Formula (I-1) are described below, but are not limited to these structures. For purposes of these structures, "$R_2$" and "X" are as defined above for Formula I-1.

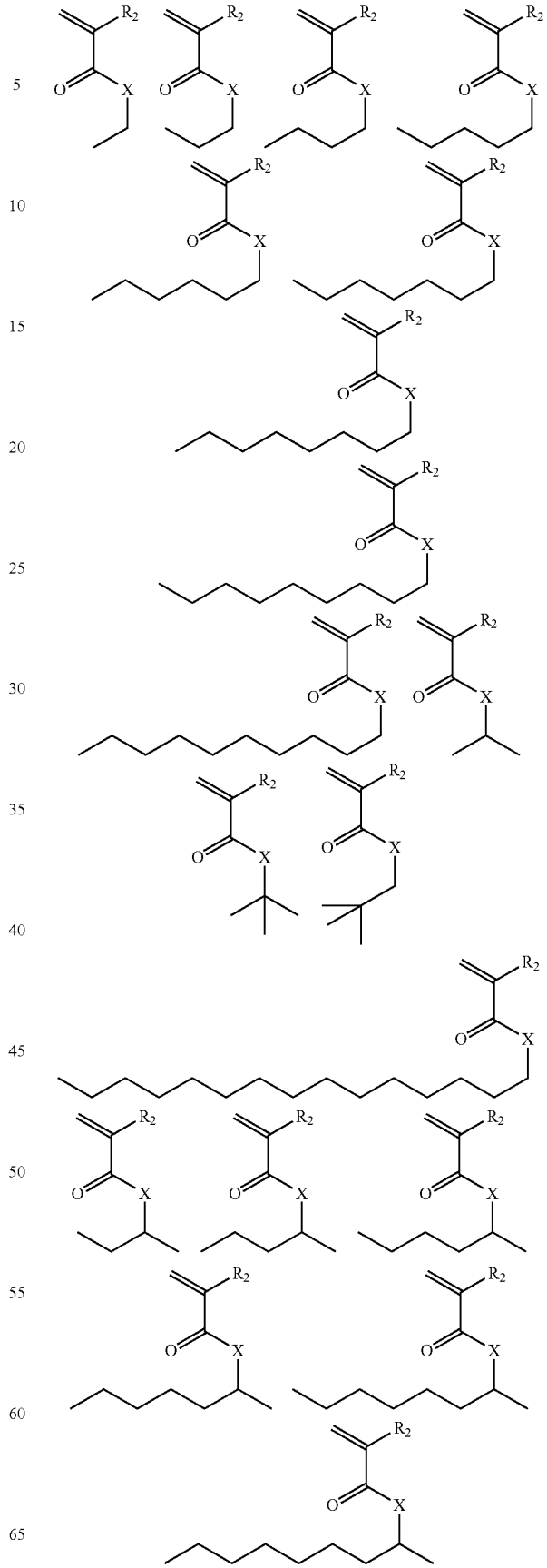

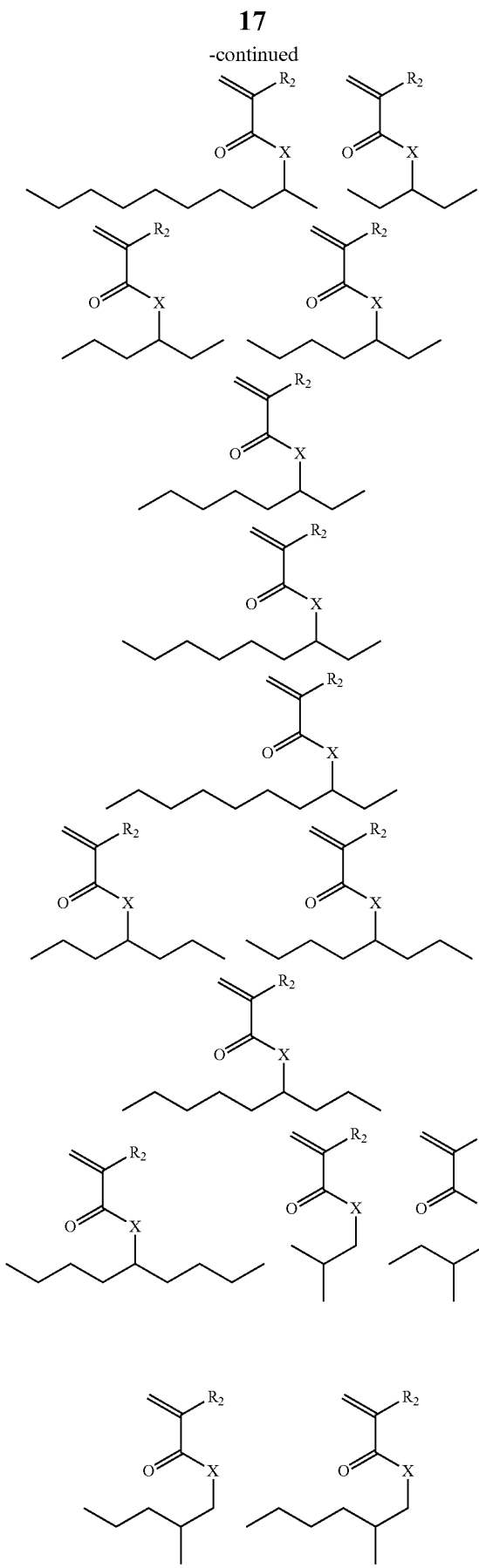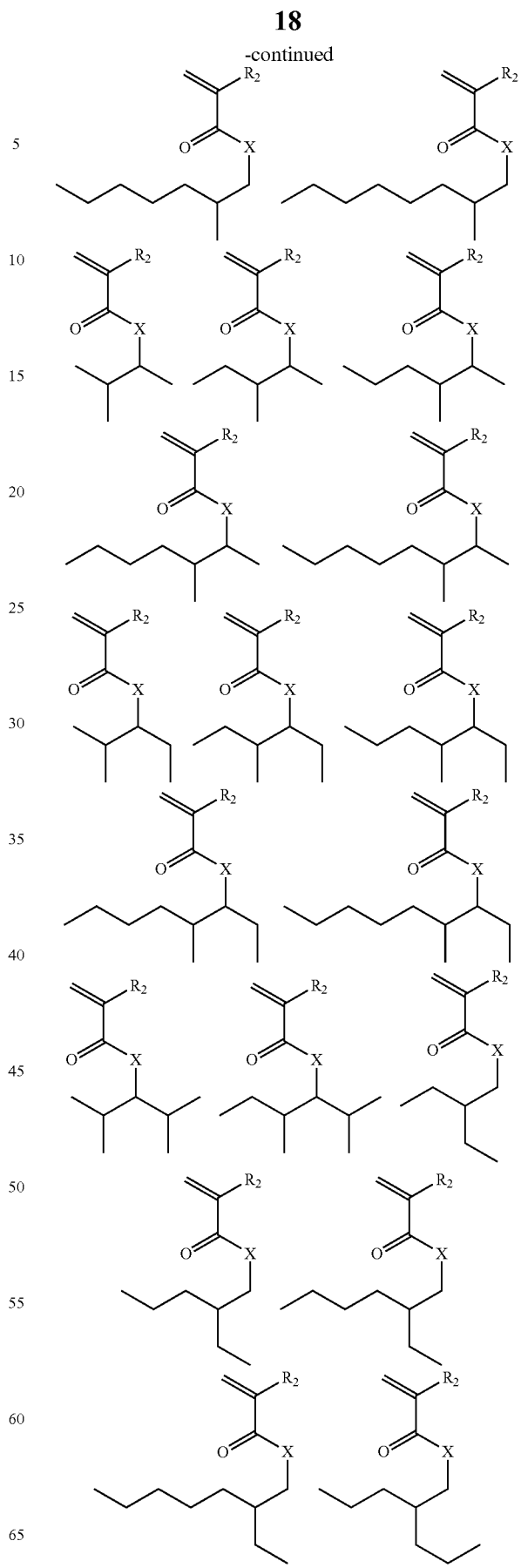

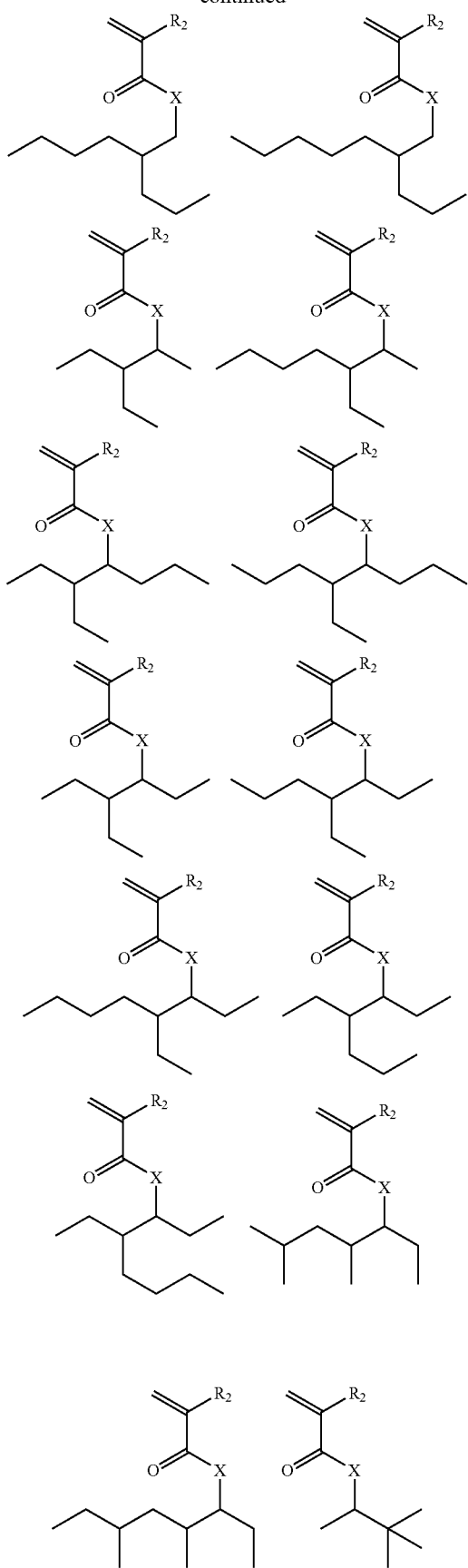
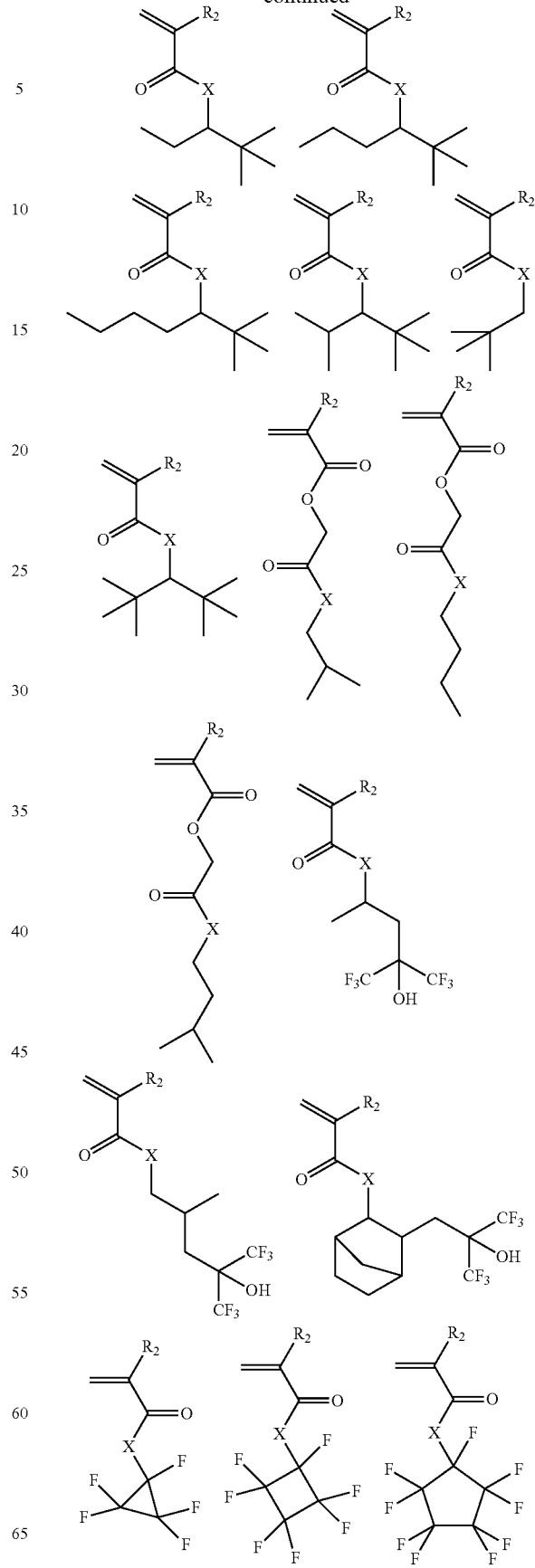

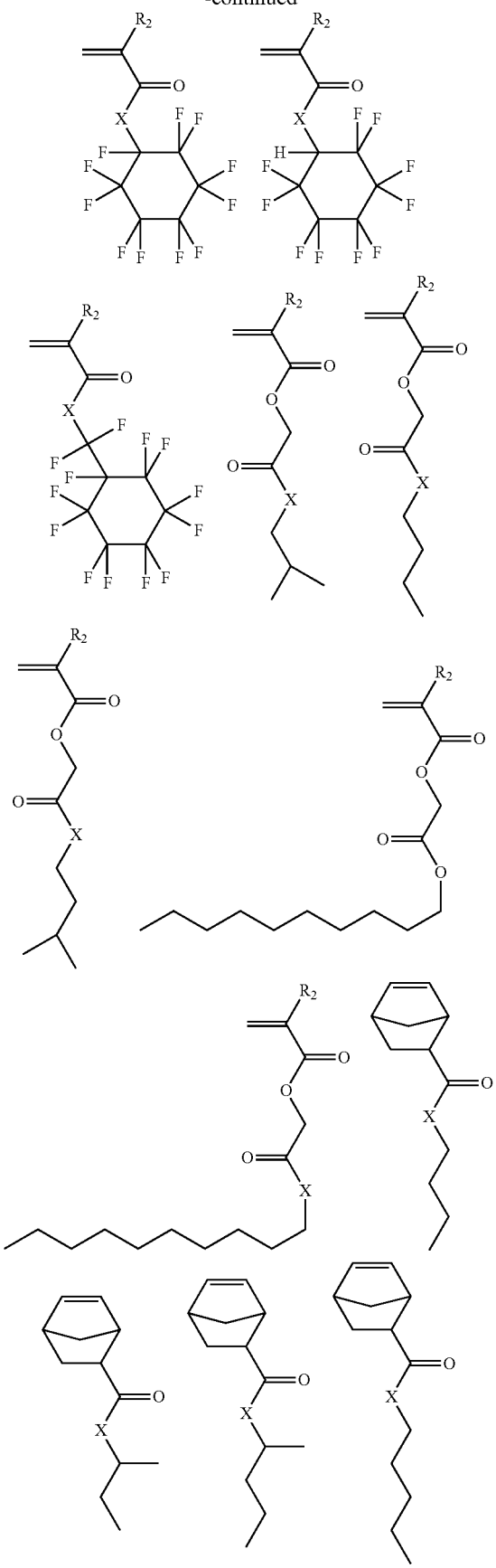
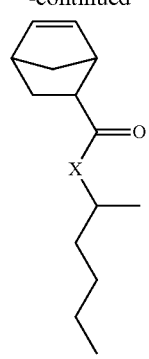
Exemplary first polymers useful in the present photoresist compositions include the following. For purposes of these structures, "$R_2$" and "X" are defined as follows: each $R_2$ is independently chosen from hydrogen, fluorine and fluorinated and non-fluorinated C1 to C3 alkyl; and each X is independently oxygen or sulfur.
$$-R_1-R_2-\cdots-R_n-X-$$
R =
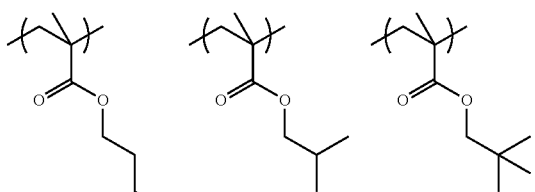
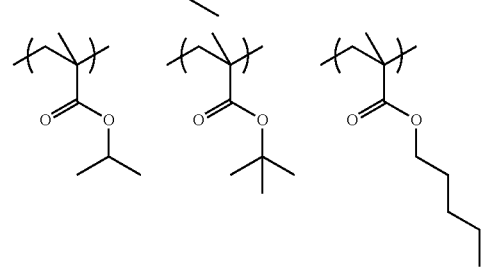
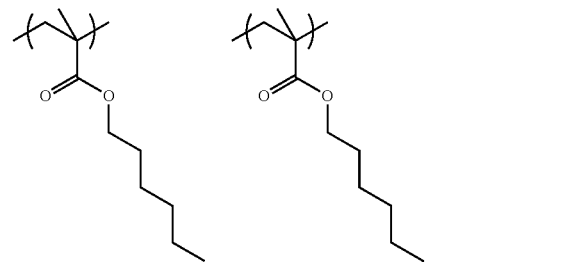

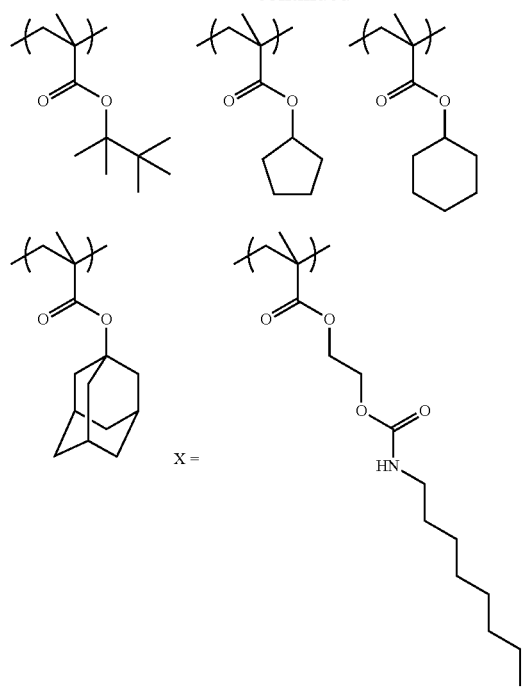
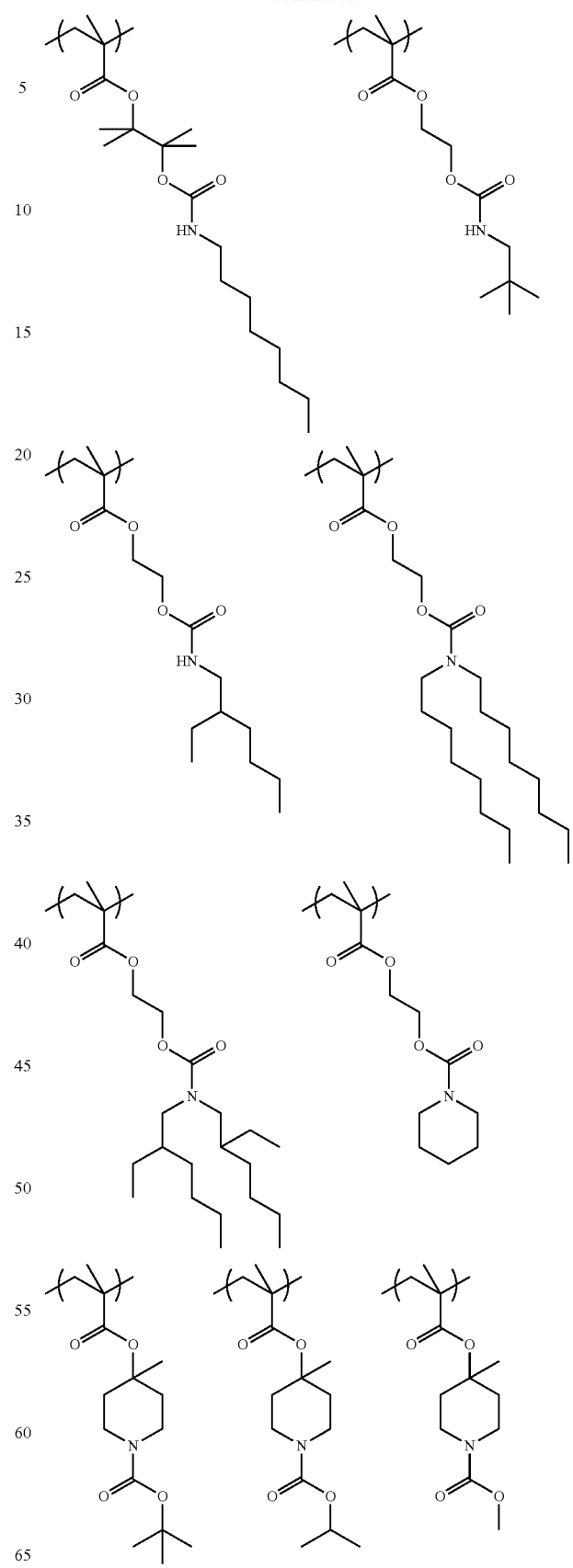

-continued

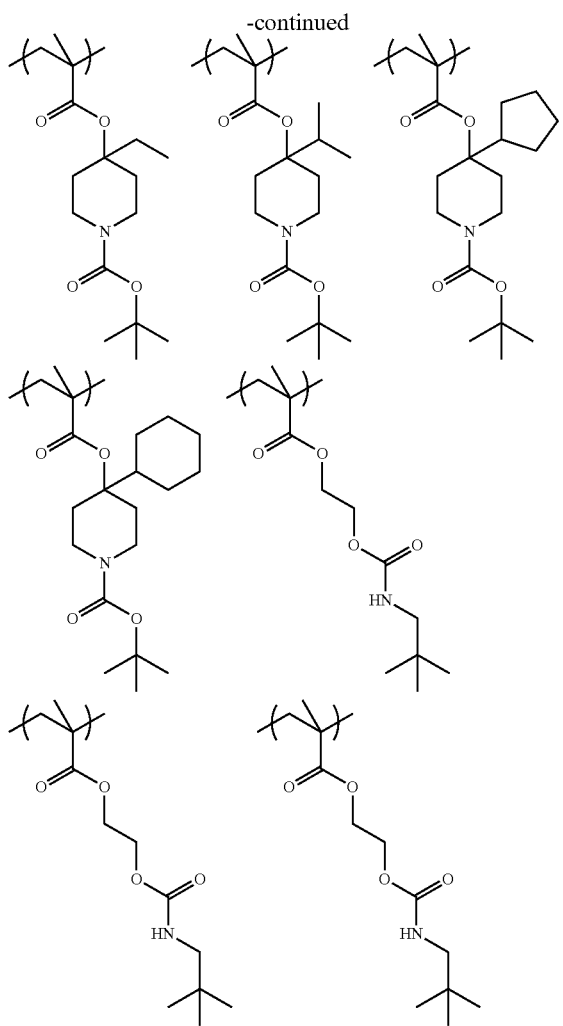

The photoresist compositions suitably include a single first polymer, but can optionally include one or more additional first polymers. Suitable polymers and monomers for use in the photoresist compositions are commercially available and/or can readily be made by persons skilled in the art.

The first polymer is typically present in the photoresist composition in a relatively small amount, for example, in an amount of from 0.1 to 10 wt %, preferably from 0.5 to 5 wt %, more preferably from 1 to 3 wt %, based on total solids of the photoresist composition. The content of the first or additive polymer will depend, for example, on the content of acid generator in the photoresist layer, the content of the nitrogen-containing groups in the first polymer, and whether the lithography is a dry or immersion-type process. For example, the first polymer lower limit for immersion lithography is generally dictated by the need to prevent leaching of the resist components. An excessively high first polymer content will typically result in pattern degradation. The weight average molecular weight of the additive polymer is typically less than 400,000, preferably from 3000 to 50,000, more preferably from 3000 to 25,000. Suitable first polymers and monomers for making the first polymers for use in the photoresist compositions of the invention are commercially available and/or can be made by persons skilled in the art.

The photosensitive composition preferably may comprise one or more photoacid generators (PAG) employed in an amount sufficient to generate a latent image in a coating layer of the photoresist composition upon exposure to activating radiation. For example, the photoacid generator will suitably be present in an amount of from about 1 to 20 wt % based on total solids of the photoresist composition. Typically, lesser amounts of the photoactive component will be suitable for chemically amplified resists.

Suitable PAGs are known in the art of chemically amplified photoresists and include, for example: onium salts, for example, triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate; nitrobenzyl derivatives, for example, 2-nitrobenzyl p-toluenesulfonate, 2,6-dinitrobenzyl p-toluenesulfonate, and 2,4-dinitrobenzyl p-toluenesulfonate; sulfonic acid esters, for example, 1,2,3-tris(methanesulfonyloxy)benzene, 1,2,3-tris(trifluoromethanesulfonyloxy)benzene, and 1,2,3-tris(p-toluenesulfonyloxy)benzene; diazomethane derivatives, for example, bis(benzenesulfonyl)diazomethane, bis(p-toluenesulfonyl)diazomethane; glyoxime derivatives, for example, bis-O-(p-toluenensulfonyl)-α-dimethylglyoxime, and bis-O-(n-butanesulfonyl)-α-dimethylglyoxime; sulfonic acid ester derivatives of an N-hydroxyimide compound, for example, N-hydroxysuccinimide methanesulfonic acid ester, N-hydroxysuccinimide trifluoromethanesulfonic acid ester; and halogen-containing triazine compounds, for example, 2-(4-methoxyphenyl)-4,6-bis(trichloromethyl)-1,3,5-triazine, and 2-(4-methoxynaphthyl)-4,6-bis(trichloromethyl)-1,3,5-triazine. One or more of such PAGs can be used.

Suitable solvents for the photoresist compositions of the invention include, for example: glycol ethers such as 2-methoxyethyl ether (diglyme), ethylene glycol monomethyl ether, and propylene glycol monomethyl ether; propylene glycol monomethyl ether acetate; lactates such as methyl lactate and ethyl lactate; propionates such as methyl propionate, ethyl propionate, ethyl ethoxy propionate and methyl-2-hydroxy isobutyrate; Cellosolve esters such as methyl Cellosolve acetate; aromatic hydrocarbons such as toluene and xylene; and ketones such as methylethyl ketone, cyclohexanone and 2-heptanone. A blend of solvents such as a blend of two, three or more of the solvents described above also are suitable. The solvent is typically present in the composition in an amount of from 90 to 99 wt %, more typically from 95 to 98 wt %, based on the total weight of the photoresist composition.

Other optional additives for the photoresist compositions include, for example, actinic and contrast dyes, anti-striation agents, plasticizers, speed enhancers, sensitizers, and the like. Such optional additives if used are typically present in the composition in minor amounts such as from 0.1 to 10 wt % based on total solids of the photoresist composition, although fillers and dyes can be present in relatively large concentrations, for example, from 5 to 30 wt % based on total solids of the photoresist composition.

A preferred optional additive of resist compositions of the invention is an added base which can enhance resolution of a developed resist relief image. Suitable basic quenchers include, for example: linear and cyclic amides and derivatives thereof such as N,N-bis(2-hydroxyethyl)pivalamide, N,N-Diethylacetamide, N1,N1,N3,N3-tetrabutylmalonamide, 1-methylazepan-2-one, 1-allylazepan-2-one and tert-butyl 1,3-dihydroxy-2-(hydroxymethyl)propan-2-ylcarbamate; aromatic amines such as pyridine, and di-tert-butyl pyridine; aliphatic amines such as triisopropanolamine, n-tert-butyldiethanolamine, tris(2-acetoxy-ethyl) amine, 2,2',2'',2'''-(ethane-1,2-diylbis(azanetriyl))tetraethanol, and 2-(dibutylamino)ethanol, 2,2',2"-nitrilotriethanol; cyclic aliphatic amines such as 1-(tert-butoxycarbonyl)-4-hydroxypiperidine, tert-butyl 1-pyrrolidinecarboxylate, tert-butyl 2-ethyl-1H-imidazole-1-carboxylate, di-tert-butyl piperazine-1,4-dicarboxylate and N (2-acetoxy-ethyl) morpholine. Of these basic quenchers, 1-(tert-butoxycarbonyl)-4-hydroxypiperidine and triisopropanolamine are preferred. The added base is suitably used in relatively small amounts, for example, from 1 to 20 wt % relative to the PAG, more typically from 5 to 15 wt % relative to the PAG.

The photoresists used in accordance with the invention are generally prepared following known procedures. For example, a resist of the invention can be prepared as a coating composition by dissolving the components of the photoresist in a suitable solvent, for example, one or more of: a glycol ether such as 2-methoxyethyl ether (diglyme), ethylene glycol monomethyl ether, propylene glycol monomethyl ether; propylene glycol monomethyl ether acetate; lactates such as ethyl lactate or methyl lactate, with ethyl lactate being preferred; propionates, particularly methyl propionate, ethyl propionate and ethyl ethoxy propionate; a Cellosolve ester such as methyl Cellosolve acetate; an aromatic hydrocarbon such toluene or xylene; or a ketone such as methylethyl ketone, cyclohexanone and 2-heptanone. The desired total solids content of the photoresist will depend on factors such as the particular polymers in the composition, final layer thickness and exposure wavelength. Typically the solids content of the photoresist varies from 1 to 10 wt %, more typically from 2 to 5 wt %, based on the total weight of the photoresist composition.

The invention further provides methods for forming a photoresist relief image and producing an electronic device using photoresists of the invention. The invention also provides novel articles of manufacture comprising substrates coated with a photoresist composition of the invention.

In lithographic processing, a photoresist composition may be applied on a variety of substrates. The substrate can be of a material such as a semiconductor, such as silicon or a compound semiconductor (e.g., III-V or II-VI), glass, quartz, ceramic, copper and the like. Typically, the substrate is a semiconductor wafer, such as single crystal silicon or compound semiconductor wafer, and may have one or more layers and patterned features formed on a surface thereof. One or more layers to be patterned may be provided over the substrate. Optionally, the underlying base substrate material itself may be patterned, for example, when it is desired to form trenches in the substrate material. In the case of patterning the base substrate material itself, the pattern shall be considered to be formed in a layer of the substrate.

The layers may include, for example, one or more conductive layers such as layers of aluminum, copper, molybdenum, tantalum, titanium, tungsten, alloys, nitrides or silicides of such metals, doped amorphous silicon or doped polysilicon, one or more dielectric layers such as layers of silicon oxide, silicon nitride, silicon oxynitride, or metal oxides, semiconductor layers, such as single-crystal silicon, and combinations thereof. The layers to be etched can be formed by various techniques, for example, chemical vapor deposition (CVD) such as plasma-enhanced CVD, low-pressure CVD or epitaxial growth, physical vapor deposition (PVD) such as sputtering or evaporation, or electroplating. The particular thickness of the one or more layers to be etched 102 will vary depending on the materials and particular devices being formed.

Depending on the particular layers to be etched, film thicknesses and photolithographic materials and process to be used, it may be desired to dispose over the layers a hard mask layer and/or a bottom antireflective coating (BARC) over which a photoresist layer is to be coated. Use of a hard mask layer may be desired, for example, with very thin resist layers, where the layers to be etched require a significant etching depth, and/or where the particular etchant has poor resist selectivity. Where a hard mask layer is used, the resist patterns to be formed can be transferred to the hard mask layer which, in turn, can be used as a mask for etching the underlying layers. Suitable hard mask materials and formation methods are known in the art. Typical materials include, for example, tungsten, titanium, titanium nitride, titanium oxide, zirconium oxide, aluminum oxide, aluminum oxynitride, hafnium oxide, amorphous carbon, silicon oxynitride and silicon nitride. The hard mask layer can include a single layer or a plurality of layers of different materials. The hard mask layer can be formed, for example, by chemical or physical vapor deposition techniques.

A bottom antireflective coating may be desirable where the substrate and/or underlying layers would otherwise reflect a significant amount of incident radiation during photoresist exposure such that the quality of the formed pattern would be adversely affected. Such coatings can improve depth-of-focus, exposure latitude, linewidth uniformity and CD control. Antireflective coatings are typically used where the resist is exposed to deep ultraviolet light (300 nm or less), for example, KrF excimer laser light (248 nm) or ArF excimer laser light (193 nm). The antireflective coating can comprise a single layer or a plurality of different layers. Suitable antireflective materials and methods of formation are known in the art. Antireflective materials are commercially available, for example, those sold under the AR™ trademark by Rohm and Haas Electronic Materials LLC (Marlborough, Mass. USA), such as AR™40A and AR™124 antireflectant materials.

A photoresist layer formed from a composition of the invention as described above is applied on the substrate. The photoresist composition is typically applied to the substrate by spin-coating. During spin-coating, in resist compositions comprising both first and second polymers as disclosed herein, the first polymer in the photoresist segregates to the upper surface of the formed resist layer typically with intermixing with the second polymer in regions immediately below the upper surface. The solids content of the coating solution can be adjusted to provide a desired film thickness based upon the specific coating equipment utilized, the viscosity of the solution, the speed of the coating tool and the amount of time allowed for spinning A typical thickness for the photoresist layer is from about 500 to 3000 Å.

The photoresist layer can next be softbaked to minimize the solvent content in the layer, thereby forming a tack-free coating and improving adhesion of the layer to the substrate. The softbake can be conducted on a hotplate or in an oven, with a hotplate being typical. The softbake temperature and time will depend, for example, on the particular material of the photoresist and thickness. Typical softbakes are conducted at a temperature of from about 90 to 150° C., and a time of from about 30 to 90 seconds.

The photoresist layer is next suitably exposed to activating radiation through a photomask to create a difference in solubility between exposed and unexposed regions. References herein to exposing a photoresist composition to radiation that is activating for the composition indicates that the radiation is capable of forming a latent image in the photoresist composition. The photomask has optically transparent and optically opaque regions corresponding to regions of the resist layer to remain and be removed, respectively, in a subsequent development step. The exposure wavelength is typically sub-400 nm, sub-300 nm or sub-200 nm, with 248 nm, 193 nm and EUV wavelengths being typical. Photoresist materials can further be used with electron beam exposure. The methods find use in immersion or dry (non-immersion) lithography techniques. The exposure energy is typically from about 10 to 80 mJ/cm$^2$, dependent upon the exposure tool and the components of the photosensitive composition.

Following exposure of the photoresist layer, a post-exposure bake (PEB) is performed. The PEB can be conducted, for example, on a hotplate or in an oven. Conditions for the PEB will depend, for example, on the particular photoresist composition and layer thickness. The PEB is typically conducted at a temperature of from about 80 to 150° C., and a time of from about 30 to 90 seconds. A latent image defined by the boundary (dashed line) between polarity-switched and unswitched regions (corresponding to exposed and unexposed regions, respectively) is formed in the photoresist. The basic moiety (e g amine) of the first polymer deprotected during the post-exppsire bake is believed to prevent polarity switch in dark regions of the photoresist layer where stray or scattered light may be present, resulting in a latent image with vertical walls. This is a result of neutralization of acid generated by the PAG in the dark regions. As a result, cleavage of the acid-labile groups in those regions can be substantially prevented.

The exposed photoresist layer is next developed suitably to remove unexposed regions of the photoresist layer. As discussed, the developer may be an organic developer, for example, a solvent chosen from ketones, esters, ethers, hydrocarbons, and mixtures thereof. Suitable ketone solvents include, for example, acetone, 2-hexanone, 5-methyl-2-hexanone, 2-heptanone, 4-heptanone, 1-octanone, 2-octanone, 1-nonanone, 2-nonanone, diisobutyl ketone, cyclohexanone, methylcyclohexanone, phenylacetone, methyl ethyl ketone and methyl isobutyl ketone. Suitable ester solvents include, for example, methyl acetate, butyl acetate, ethyl acetate, isopropyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate and propyl lactate. Suitable ether solvents include, for example, dioxane, tetrahydrofuran and glycol ether solvents, for example, ethylene glycol monomethyl ether, propylene glycol monomethyl ether, ethylene glycol monoethyl ether, propylene glycol monoethyl ether, diethylene glycol monomethyl ether, triethylene glycol monoethyl ether and methoxymethyl butanol. Suitable amide solvents include, for example, N-methyl-2-pyrrolidone, N,N-dimethylacetamide and N,N-dimethylformamide. Suitable hydrocarbon solvents include, for example, aromatic hydrocarbon solvents such as toluene and xylene. In addition, mixtures of these solvents, or one or more of the listed solvents mixed with a solvent other than those described above or mixed with water can be used. Other suitable solvents include those used in the photoresist composition. The developer is preferably 2-heptanone or a butyl acetate such as n-butyl acetate.

Mixtures of organic solvents can be employed as a developer, for example, a mixture of a first and second organic solvent. The first organic solvent can be chosen from hydroxy alkyl esters such as methyl-2-hydroxyisobutyrate and ethyl lactate; and linear or branched $C_5$ to $C_6$ alkoxy alkyl acetates such as propylene glycol monomethyl ether acetate (PGMEA). Of the first organic solvents, 2-heptanone and 5-methyl-2-hexanone are preferred. The second organic solvent can be chosen from linear or branched unsubstituted $C_6$ to $C_8$ alkyl esters such as n-butyl acetate, n-pentyl acetate, n-butyl propionate, n-hexyl acetate, n-butyl butyrate and isobutyl butyrate; and linear or branched $C_8$ to $C_9$ ketones such as 4-octanone, 2,5-dimethyl-4-hexanone and 2,6-dimethyl-4-heptanone. Of the second organic solvents, n-butyl acetate, n-butyl propionate and 2,6-dimethyl-4-heptanone are preferred. Preferred combinations of the first and second organic solvent include 2-heptanone/n-butyl propionate, cyclohexanone/n-butyl propionate, PGMEA/n-butyl propionate, 5-methyl-2-hexanone/n-butyl propionate, 2-heptanone/2,6-dimethyl-4-heptanone and 2-heptanone/n-butyl acetate. Of these, 2-heptanone/n-butyl acetate and 2-heptanone/n-butyl propionate are particularly preferred.

The organic solvents are typically present in the developer in a combined amount of from 90 wt % to 100 wt %, more typically greater than 95 wt %, greater than 98 wt %, greater than 99 wt % or 100 wt %, based on the total weight of the developer.

The developer material may include optional additives, for example, surfactants such as described above with respect to the photoresist. Such optional additives typically will be present in minor concentrations, for example, in amounts of from about 0.01 to 5 wt % based on the total weight of the developer.

The developer is typically applied to the substrate by spin-coating. The development time is for a period effective to remove the unexposed regions of the photoresist, with a time of from 5 to 30 seconds being typical. Development is typically conducted at room temperature. The development process can be conducted without use of a cleaning rinse following development. In this regard, it has been found that the development process can result in a residue-free wafer surface rendering such extra rinse step unnecessary.

The BARC layer, if present, is selectively etched using resist pattern as an etch mask, exposing the underlying hardmask layer. The hardmask layer is next selectively etched, again using the resist pattern as an etch mask, resulting in patterned BARC and hardmask layers. Suitable etching techniques and chemistries for etching the BARC layer and hardmask layer are known in the art and will depend, for example, on the particular materials of these layers. Dry-etching processes such as reactive ion etching are typical. The resist pattern and patterned BARC layer are next removed from the substrate using known techniques, for example, oxygen plasma ashing.

The following non-limiting examples are illustrative of the invention.

EXAMPLES

Example 1: Synthesis of Monomer A

Scheme: Monomer A

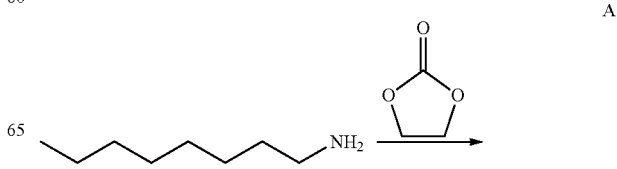

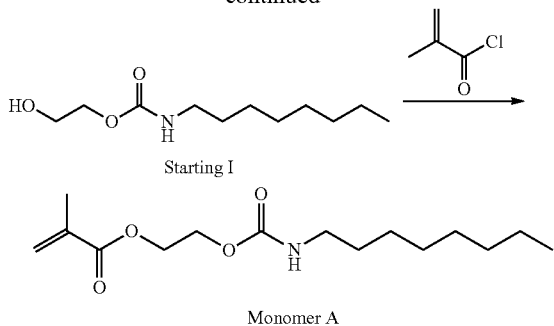

Starting I

Monomer A n-Octylamine(10.0 g, 0.07743 mol) and ethylene carbonate(6.883 g, 0.0782 mol) were charged into round-bottom flask. The mixture was stirred at 100° C. for 2 h. The reaction mixture was cooled to room temperature and filtered. The 16.3 g of product(Starting I) was obtained.

Starting I (10.0 g, 0.0461 mol) and triethylamine(19.24 mL, 0.138 mol) were dissolved in 100 mL of dry methylene chloride into round-bottom flask under nitrogen atmosphere. Methacryloyl chloride(5.82 mL, 0.0599 mol) was added dropwisely at 0° C. The reaction mixture was slowly warmed up to room temperature and allowed to stir at this temperature for 3 h.

The reaction mixture was transferred to 100 mL of deionized water and the organic phase was washed with an aqueous NH$_4$Cl and deionized water consecutively, The collected organic solution was dried over sodium sulfate, filtered and concentrated in vacuo. The 11.3 g of product (Monomer A as depicted I above Scheme) was obtained.

Example 2: Synthesis of Monomer B 1-(tert-Butoxycarbonyl)-4-piperidone(15.00 g, 0.0753 mmol) were dissolved in 300 mL of diethyl ether into round-bottom flask under nitrogen atmosphere. The resulting solution was cooled to −40° C. and 3 M solution of ethyl magnesium bromide (32.64 mL, 0.0979 mmol) in diethyl ether was added. The reaction was allowed to stir at −30-40° C. for 30 min, then slowly warmed up to room temperature and stirred an additional 6 h. The reaction was quenched by slow addition of H$_2$O and the resulting mixture was transferred to 200 mL of deionized water and the organic phase was washed with saturated NH$_4$Cl. and the organic phase was washed with saturated NH$_4$Cl and deionized water consecutively, The collected organic solution was dried over sodium sulfate, filtered and concentrated in vacuo. The 12.2 g of product (Starting II) was obtained.

Starting II (shown in the above Scheme—0.0 g, 0.0436 mol) and triethylamine(18.23 mL, 0.131 mol) were dissolved in 100 mL of methylene chloride into round-bottom flask under nitrogen atmosphere. Methacryloyl chloride(5.5 mL, 0.0567 mol) was added dropwisely at 0° C. The reaction mixture was slowly warmed up to room temperature and allowed to stir at this temperature for 3 h.

The reaction mixture was transferred to 100 mL of deionized water and the organic phase was washed with an aqueous NH$_4$Cl and deionized water consecutively, The collected organic solution was dried over sodium sulfate, filtered and concentrated in vacuo. 9.6 g of product TBPEMA (Monomer B as shown in the above) was obtained.

Example 3: Synthesis of Polymer B

Scheme: Monomer B

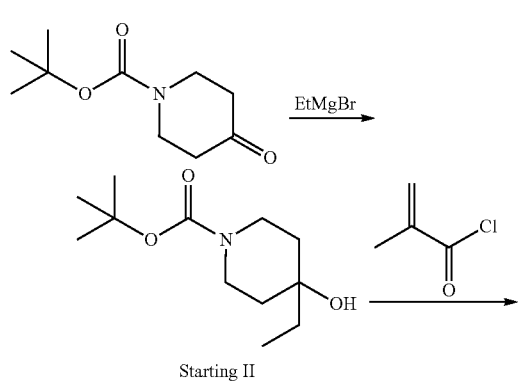

Starting II

Monomer B

Scheme: Polymer B

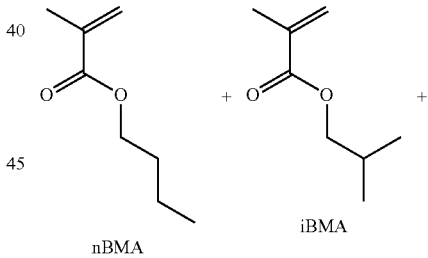

nBMA        iBMA

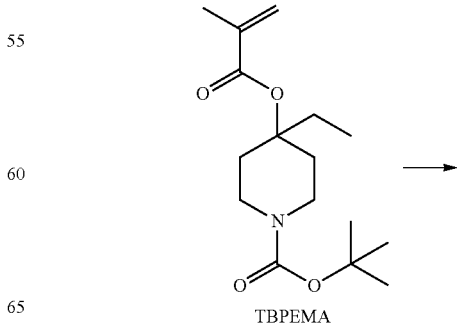

TBPEMA

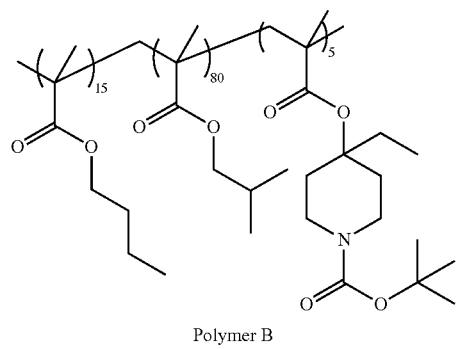

Polymer B

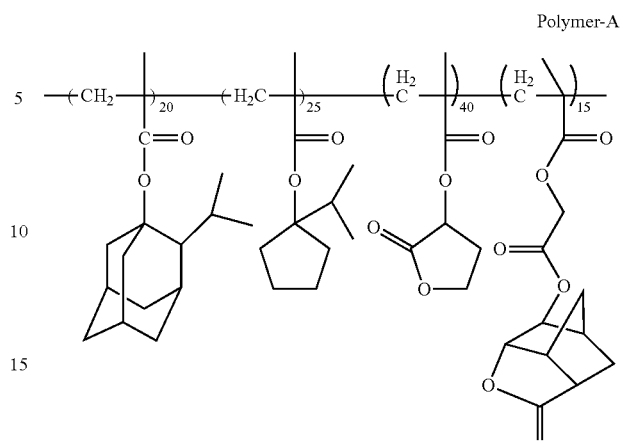

IPAMA/IPCPMA/aGBLMA/MNLMA
(20/25/40/15)

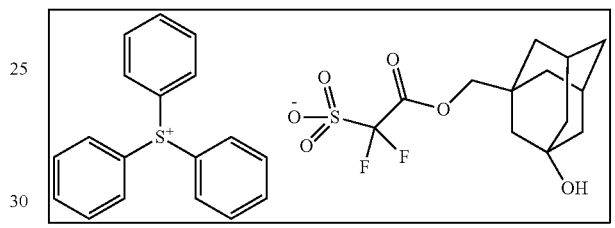

PAG-A

A series of monomers, nBMA (2.85 g), iBMA (15.17 g) and of TBPEMA (1.98 g) were dissolved in 16.333 g of PGMEA in round-bottom flask at room temperature with stirring and degassed with nitrogen for 20 min PGMEA (30.333 g) was charged into a Julabo reactor equipped with a condenser and a mechanical stirrer. After degassed with nitrogen for 20 min. The solvent in the Julabo reactor was heated up to 80° C. In other round-bottom flask, the initiator V601 (3.64 g) was dissolved in 5.47 g of PGMEA and degassed with nitrogen for 20 min. The initiator solution was added slowly into the Julabo reactor and stirred for 15 min the monomer solution was fed into the Julabo reactor dropwisely over the 3 hours with rigorous stirring under nitrogen environment. After monomer feeding was completed, the reaction mixture was stirred for an hour at 80° C. The reaction mixture was allowed to cool down to room temperature to methanol and water solvent mixture (865 g) with 8 to 2 ratios. The precipitated polymer was collected by filtration and dried in air overnightly, The dried polymer was re-dissolved in 46.7 g of THF and re-precipitated in methanol and water solvent mixtures (667 g) with 8 to 2 ratios. The final polymer was filtered, and dried in air overnightly and under vacuum at 50° C. for 24 hours to give 12.4 g of poly(nBMA/iBMA/TBPMA) (14.7/80.8/4.5) Polymer B shown in the above Scheme (Mw=5690 and PDI=1.42).

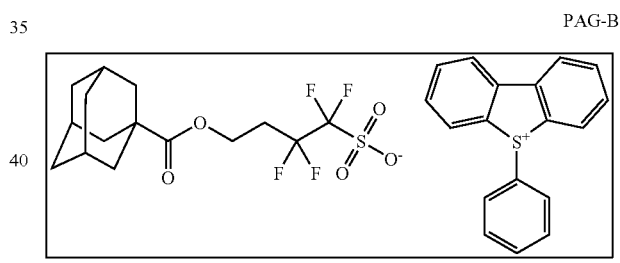

PAG-B

Example 4: Preparation of Photoresist Composition

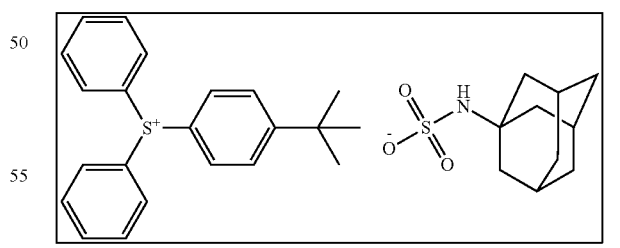

WPAG

A photoresist composition of the invention is prepared by admixing the following components, 53.87 g polymer-A solution (15%) in PGMEA, 54.29 g PAG-A solution (1%) in methyl-2-hydroxyisobutyrate, 17.97 g PAG-B solution (1%) in methyl-2-Hydroxyisobutyrate, 8.91 g WPAG solution (2%) in methyl-2-hydroxyisobutyrate, 13.30 g Quencher-A solution (1%) in PGMEA, 3.72 g EBL-A (5%) in PGMEA, 82.86 g PGMEA, 29.07 g gamma-butyrolactone and 36.00 g methyl-2-hydroxyisobutyrate and then this mixture was filtered with a 0.2 micron Nylon filter.

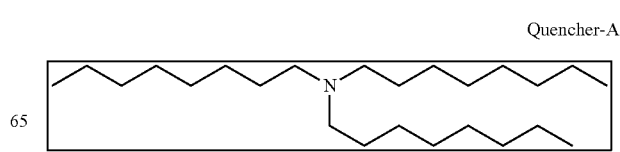

Quencher-A

EBL-A

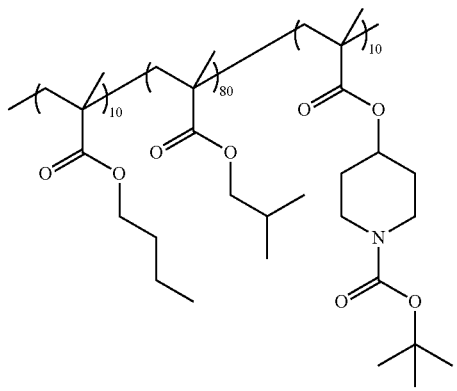

Example 5: Preparation of Photoresist Composition

A photoresist composition of the invention is prepared by admixing the following components, 53.87 g polymer-A solution (15%) in PGMEA, 54.29 g PAG-A solution (1%) in methyl-2-hydroxyisobutyrate, 17.97 g PAG-B solution (1%) in methyl-2-Hydroxyisobutyrate, 8.91 g WPAG solution (2%) in methyl-2-hydroxyisobutyrate, 13.30 g Quencher-A solution (1%) in PGMEA, 3.72 g EBL-B (5%) in PGMEA, 82.86 g PGMEA, 29.07 g gamma-butyrolactone and 36.00 g methyl-2-hydroxyisobutyrate and then this mixture was filtered with a 0.2 micron Nylon filter.

Polymer-A

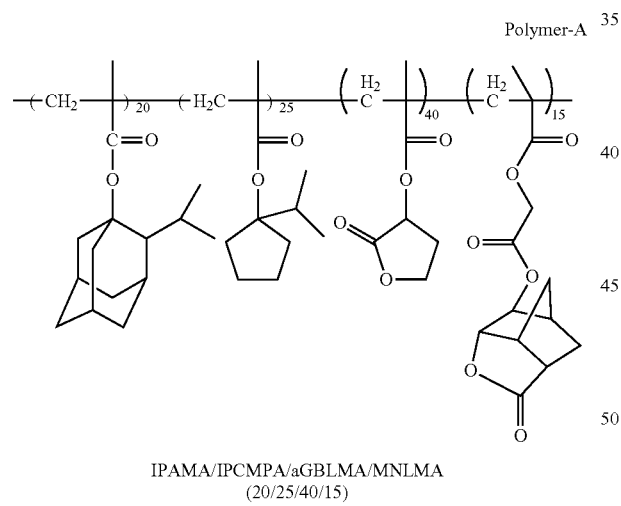

IPAMA/IPCMPA/aGBLMA/MNLMA
(20/25/40/15)

PAG-A

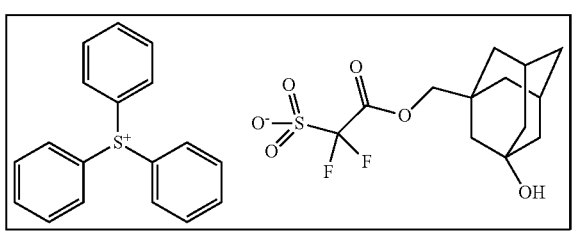

PAG-B

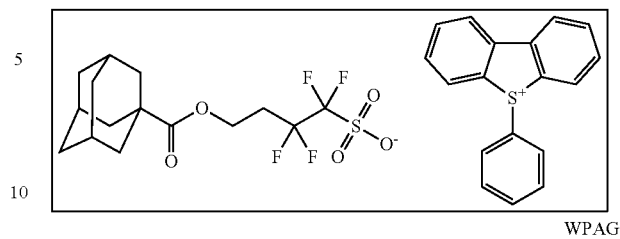

WPAG

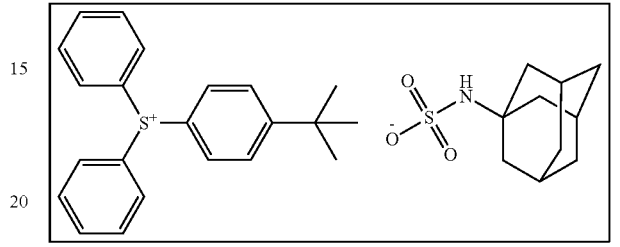

Quencher-A

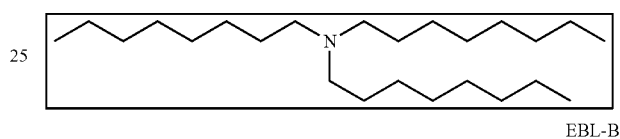

EBL-B

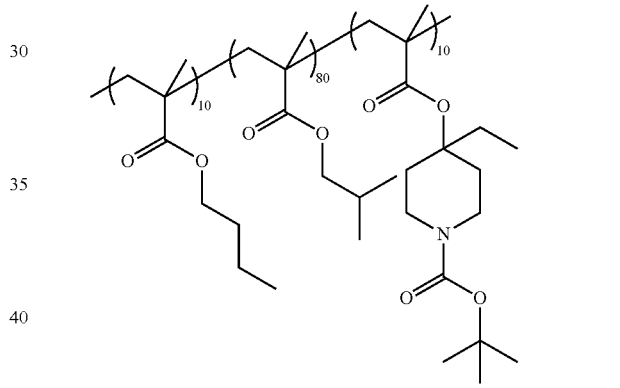

Example 6: Lithography 300 mm HMDS-primed silicon wafers are spin-coated with AR™26N (Rohm and Haas Electronic Materials) to form a first bottom anti-reflective coating (BARC) on a TEL CLEAN TRAC LITHIUS i+, followed by the bake process for 60 seconds at 205° C.

A photoresist composition of Example 5 is spin-coated over the BARC layer. The thus applied photoresist layer is then soft-baked and imaged in an immersion lithography system with patterned radiation having a wavelength of 193 nm. The exposed wafers are post-exposure baked at 90° C. for 60 seconds and then developed using n-butyl acetate developer for approximately 30 seconds to give negative tone patterns of the photoresist.

What is claimed is:
1. A photoresist composition comprising:
(a) a first polymer comprising:
first units comprising a reactive nitrogen-containing moiety spaced from the polymer backbone, wherein the nitrogen-containing moiety produces a basic cleavage product during lithographic processing of the photoresist composition; and
second units each comprising 1) a reactive nitrogen-containing moiety and 2) an acid-labile group;
(b) a second polymer distinct from the first polymer; and
(c) one or more acid generators,
wherein an acid-labile moiety is interposed between the polymer backbone of the first polymer and the reactive nitrogen-containing moiety.

2. A photoresist composition of claim 1 wherein the nitrogen-containing moiety is spaced from the polymer by optionally substituted alkylene, optionally substituted carbon alicyclic, optionally substituted heteroalicyclic, optionally substituted carbocyclic aryl or optionally substituted heteroaryl.

3. The photoresist composition of claim 1 wherein the first polymer further comprises:
third units that 1) comprise one or more hydrophobic groups and 2) are distinct from both of the first and second units.

4. The photoresist composition of claim 1 wherein the nitrogen-containing moiety is a protected amine.

5. The photoresist composition of claim 1 wherein the nitrogen-containing moiety is a carbamate or sulfamate.

6. The photoresist of claim 1 wherein the second polymer comprises acid-labile groups.

7. The photoresist of claim 1 wherein the second polymer comprises acid-labile groups.

8. The photoresist of claim 1 wherein the first polymer and second polymer have differing surface energies.

9. The photoresist of claim 1 wherein the first polymer and second polymer are substantially non-miscible.

10. The photoresist of claim 1 wherein the first polymer comprises repeat units that comprise a structure obtainable by reaction of one of more of the following:

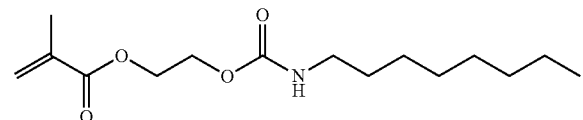

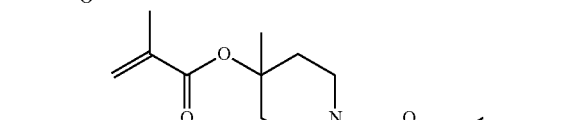

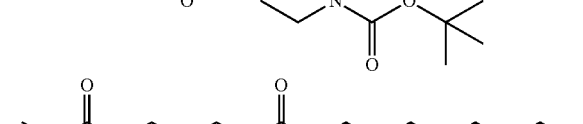

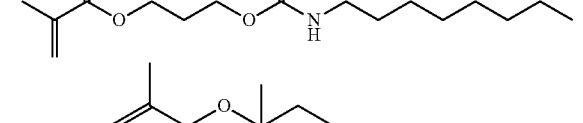

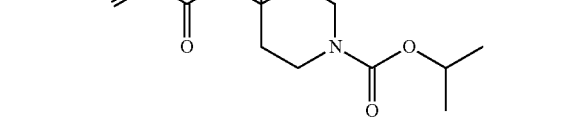

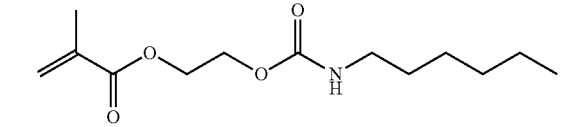

-continued

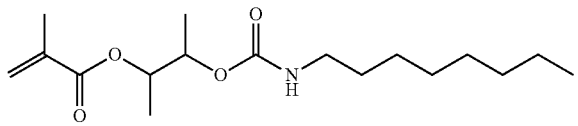

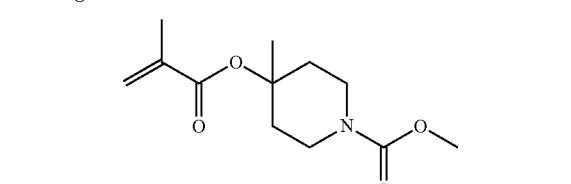

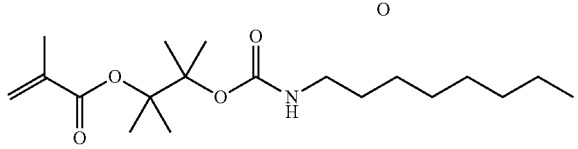

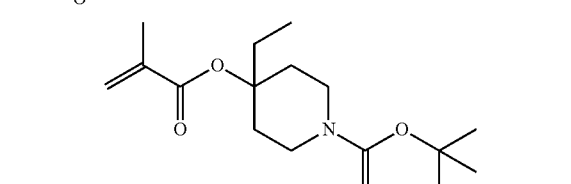

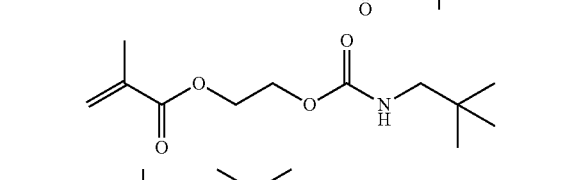

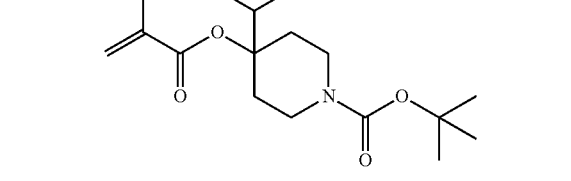

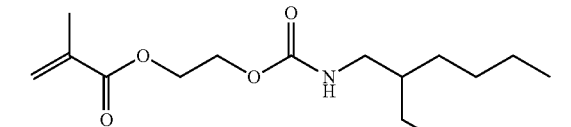

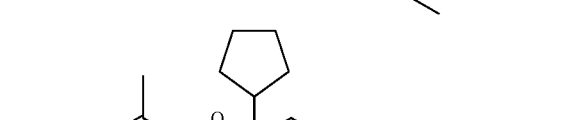

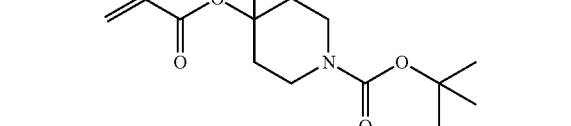

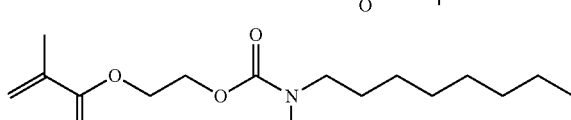

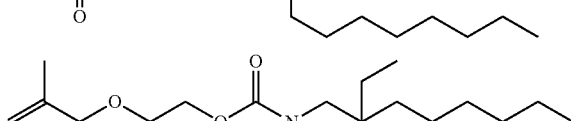

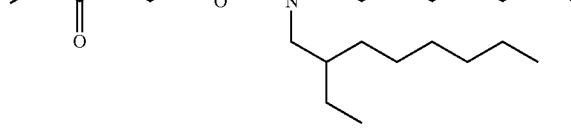

-continued
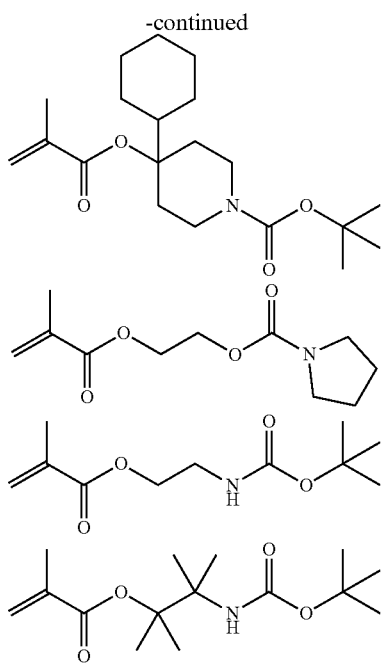
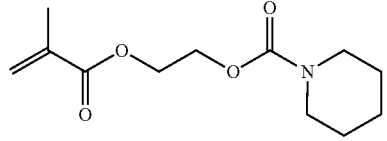
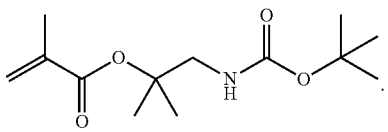
11. A method for forming a photolithographic pattern, comprising:
(a) applying a layer of a photoresist composition of claim 1 on a substrate;
(b) patternwise exposing the photoresist composition layer to activating radiation; and
(c) developing the exposed photoresist composition layer to provide a photoresist relief image.
* * * * *